(12) United States Patent
Fukui

(10) Patent No.: US 7,142,917 B2
(45) Date of Patent: Nov. 28, 2006

(54) HEART TREATMENT EQUIPMENT AND METHOD FOR PREVENTING FATAL ARRHYTHMIA

(75) Inventor: Yoshihito Fukui, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 133 days.

(21) Appl. No.: 10/725,483

(22) Filed: Dec. 3, 2003

(65) Prior Publication Data

US 2004/0215289 A1 Oct. 28, 2004

(30) Foreign Application Priority Data

Dec. 4, 2002 (JP) ............................. 2002-352373
Mar. 14, 2003 (JP) ............................. 2003-070740

(51) Int. Cl.
*A61N 1/365* (2006.01)

(52) U.S. Cl. .......................................... 607/14; 607/17

(58) Field of Classification Search ................... 607/9, 607/2, 42
See application file for complete search history.

(56) References Cited

U.S. PATENT DOCUMENTS

| | | | |
|---|---|---|---|
| 4,928,688 A | 5/1990 | Mower | |
| 5,199,428 A * | 4/1993 | Obel et al. | 607/44 |
| 5,330,507 A | 7/1994 | Schwartz | |
| 5,578,061 A | 11/1996 | Stroetmann et al. | |
| 5,658,318 A | 8/1997 | Stroetmann et al. | |
| 5,683,427 A * | 11/1997 | Ekwall | 607/11 |
| 6,073,048 A * | 6/2000 | Kieval et al. | 607/17 |
| 6,141,590 A | 10/2000 | Renirie et al. | |
| 6,415,183 B1 * | 7/2002 | Scheiner et al. | 607/42 |
| 2001/0005790 A1 | 6/2001 | Ripart | |
| 2002/0082660 A1 | 6/2002 | Andrew et al. | |
| 2003/0045909 A1 * | 3/2003 | Gross et al. | 607/9 |
| 2003/0229380 A1 * | 12/2003 | Adams et al. | 607/9 |

FOREIGN PATENT DOCUMENTS

| | | | |
|---|---|---|---|
| EP | 0 110 509 A | | 6/1984 |
| EP | 0 547 734 B | | 6/1993 |
| EP | 0 688 578 B | | 12/1995 |
| EP | 0 688 579 B | | 12/1995 |
| EP | 1 142 608 | | 10/2001 |
| WO | WO 93/02744 | * | 2/1993 |
| WO | WO 93/21824 A | | 11/1993 |
| WO | WO 01/76689 A | | 10/2001 |

OTHER PUBLICATIONS

T. Nakajima et al. "The mechanism of catecholaminergic polymorphic ventricular tachycardia may be triggered activity due to delayed after depolarization", European Heart Journal, England, Mar. 1997, pp. 530-531.

* cited by examiner

*Primary Examiner*—Robert E. Pezzuto
*Assistant Examiner*—Jessica L. Reidel
(74) *Attorney, Agent, or Firm*—Buchanan Ingersoll & Rooney PC

(57) ABSTRACT

In order to avoid a sudden cardiac death by a fatal arrhythmia, various living body information for generating a signal which shows a level of an autonomic tone is detected by a sensor or a VT/VF risk event is detected so as to control the stimulation of the vagus nerve or the nerve stimulation waveform. For this purpose, the parameter of the nerve stimulation signal is controlled according to a detection of the living body information represented by a QT interval which is measured by intracardiac information of the heart or a detection of a VT/VF risk event represented by a ventricular premature contraction which is picked up from spontaneous cardiac events.

15 Claims, 24 Drawing Sheets

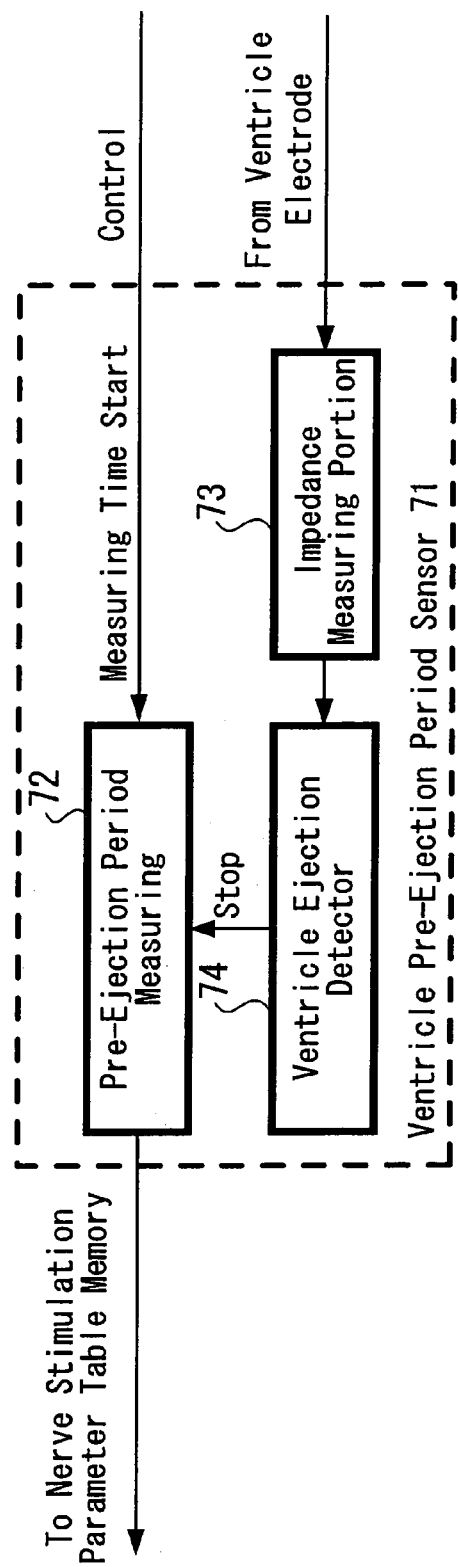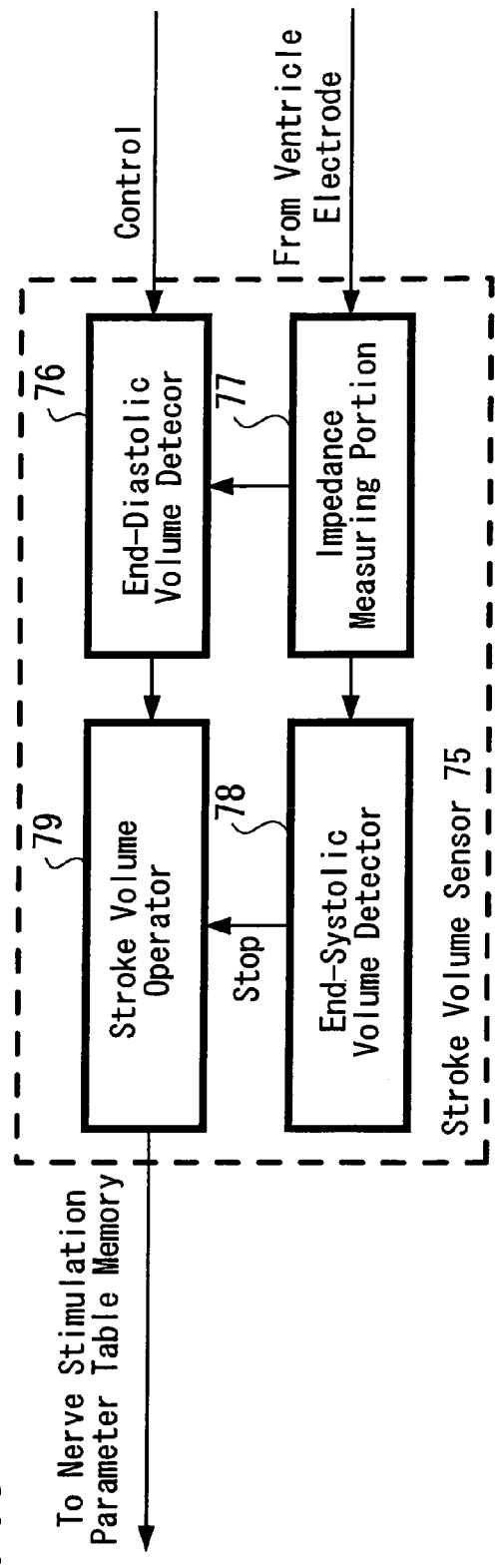

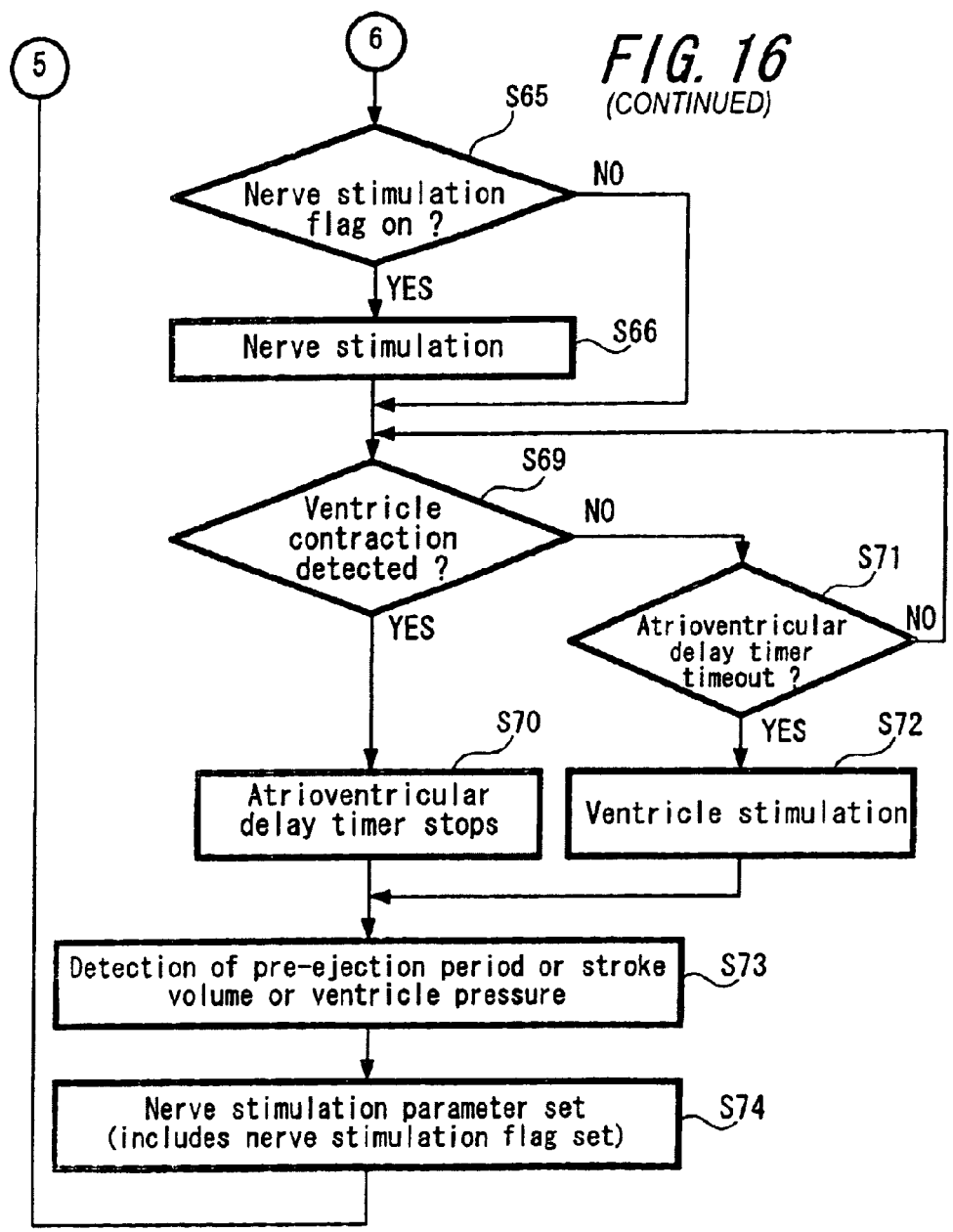

HEART TREATMENT EQUIPMENT AND METHOD FOR PREVENTING FATAL ARRHYTHMIA

BACKGROUND OF THE INVENTION

1. Field of the Invention

The present invention relates to a heart treatment equipment and method for preventing a sudden cardiac death caused by a fatal arrhythmia in patients with an organic heart disease.

2. Description of the Related Art

FIGS. 17A and 17B show a constitutional diagram of a heart and an electrocardiogram waveform respectively. A heart is constituted by two atriums and two ventricles. The atriums are chambers for storing the returned blood and the ventricles are chambers for ejecting the blood. With respect to the blood, the venous blood enters the right atrium through a large vein and is sent to a pulmonary artery passing through the right atrium and the right ventricle. The arterial blood which takes in oxygen in lungs goes into a left atrium through the pulmonary vein and is sent to the aorta passing through the left atrium and the left ventricle. The thickness of the ventricle is thicker than that of the atrium, and additionally, in order to prevent backflow of the blood, valves are provided between the right atrium and the right ventricle, between the right ventricle and the pulmonary artery, between the left atrium and the left ventricle and between the left ventricle and the aorta respectively. The condition where the heart loses its ability to maintain adequate blood circulation in the peripheral tissues and the lungs is a heart failure and in many cases, left heart failure where the pumping ability of the left ventricle is primarily affected.

Though there are individual differences, the beating of the heart counts about 100,000 times in a day. Then, a weak current is emitted every beat of the heart, so that it is possible to know the condition of the heart by detecting this current. An electrocardiogram of FIG. 17B shows a time course of the electrical activity of the normal heart. This electrocardiogram is obtained from electrodes placed on the skin in specific locations and is consisting of a plurality of waves which have amplitudes of several millivolts. As shown in the drawing, first, a wave which comes first is a P wave and this represents a current in a case when the atria (the right atrium and left atrium) depolarize. The wave which comes next is a wave called as a QRS complex and this is a wave of ventricular depolarization.

A PQ interval begins at the onset of the P wave and to the onset of the QRS complex and represents the time between the start of atrial depolarization and the start of the ventricular depolarization. A QT interval begins at the onset of the QRS complex and to the end of the T wave and represents the time between the start of ventricular depolarization and the end of ventricular repolarization.

A sudden death especially caused by a heart disease is called a sudden cardiac death and the number thereof reaches about annual 50,000 people in Japan. The immediate cause of the sudden cardiac death is the life-threatening ventricle tachycardia or the ventricle fibrillation and which is called a fatal arrhythmia. When the ventricle tachycardia which is defined as a heart rate over 100 beats/min or the ventricle fibrillation which is extremely rapid chaotic heartbeat occurs, the pumping function of the heart lowers or disappears and it becomes impossible to fill with enough blood to supply the whole body with the oxygen rich blood that it needs. For this reason, unconsciousness is caused in accordance with the decrease in the cerebral blood flow, so that a death might be caused unless an immediately appropriate treatment is conducted. The organic heart disease patients who are suffered with myocardial infarction, cardiomyopathy and the like are at high risk of the ventricle tachycardia and the ventricle fibrillation.

For a patient having a risk of such a sudden cardiac death, an implantable cardioverter defibrillator (ICD) is used. When a ventricle tachycardia or a ventricle fibrillation is detected, the ICD delivers a shock to the heart in order to interrupt the rapid heart rhythm and restore a more normal rhythm. However, a high-energy shock is required for defibrillation and there is a danger that the cardiac tissue subjected to the shock could be damaged.

Moreover, an anti-arrhythmic medicine is generally used in order to prevent a sudden cardiac death. Especially, for the organic heart disease patients with reduced left ventricle function, it is being confirmed by cardiovascular trials in the United States that a β-blocker medicine or a class III anti-arrhythmic medicine with a β-blockade effect has an effect on the reduction of mortality. The β-blocker medicine has an effect on mainly lowering a heart rate and is effective for suppressing a rapid heart rate.

In this way, by lowering the heart rate, it is possible to reduce the number of the risk event which includes a ventricle tachycardia or a ventricle fibrillation such as a ventricular premature contraction and the like and additionally, by the decrease of the oxygen consumption of the cardiac muscle owing to the lowering of the heart rate, it is considered that it is possible to prevent a myocardial infaction and at the same time prevent a myocardial failure region and its peripheral region from becoming oxygen-deprived.

Now, the cardiac activity is put under the control of an autonomic nerve system and the autonomic nerve system has a sympathetic nerve system and a parasympathetic nerve system where the parasympathetic nerve system of the heart is a vagus nerve. The activities in the sympathetic nerve and the vagus nerve are usually antagonistic each other. The cardiac activity. (mainly heart rate and contractility) increases when the sympathetic tone increases and the cardiac activity (mainly heart rate) decreases when the vagal tone increases.

More specifically, the increase in the sympathetic tone has an excitatory effect on the cardiac activity and on the other hand, the increase in the vagal tone has an inhibitory effect on the cardiac activity. When the sympathetic tone is activated and the sympathetic tone is made to be high, a possibility of a fatal arrhythmia increases. The sympathetic tone is generally activated by physical stress or mental stress. The β-blocker medicine acts on the sympathetic nerve and makes the tone thereof calm down, so that it is considered that it is effective to prevent the fatal arrhythmia.

Additionally, it is known that the electrical stimulation of the vagus nerve exerts a similar action as the blocker medicine. Based on this principle, a method was proposed where the tachyarrhythmia is prevented or stopped by electrically stimulating the vagus nerve when a tachyarrhythmia is detected (see, for example, the specification of JP OP 8-38625).

Further, an equipment for detecting an arrhythmia in response to an activity of a nerve signal which transmits information from the autonomic nerve system to the heart has been also proposed (see, for example, the specification of JP OP 8-52121). This arrhythmia detecting equipment comprises a sensor for detecting a nerve activity and a comparator provided with a threshold value for forming a condition with reference to an existence of the arrhythmia wherein the comparator outputs an output which shows a generation of the arrhythmia depending on whether or not the nerve activity is in conformity to the condition. More specifically, the vagus nerve is lightly activated for 5 seconds immediately after an impeding fibrillation or some other dangerous impeding tachyarrhythmia is detected based on a change in the activity of an autonomic nerve system and the like. Then, the treatment will be terminated when detecting a return to a normal state of the heart and the treatment will continue, supplemented with blocking of the sympathetic nerve, preferably at the ganglion stellatum for a few seconds when detecting an abnormal condition for the heart continuously. In a case when the heart activity drops below a given rate owing to a fact that a current is supplied to the vagus nerve and the sympathetic nerve, the pacemaker block starts the stimulation of the heart automatically in order to maintain or restore its sinus rhythm.

Furthermore, in order to avoid the fatal arrhythmia, it is proposed a method and an equipment where an electrical stimulation is applied to the vagus nerve (see, for example, WO93/21824 <PCT/US93/00051>). In this equipment for treating the arrhythmia, it is directed to prevent a tachycardia or a fibrillation beforehand by detecting an ST segment change (voltage) of the patient's electrogram and by emitting a trigger for a nerve stimulation whether or not the ST value exceeds the threshold value. Further, an appropriate function of the heart would be maintained by means of the stimulation of the heart and the stimulation of the vagus nerve. This heart treatment equipment not only compares a pre-set interval threshold for detecting the tachycardia with the cardiac interval of the patient, but also carefully examines the ST segment change (voltage) of the electrogram indicative of an acute myocardial ischemia and other contributing factors relating to the ventricle tachycardia such that it becomes possible to prevent the tachycardia based on that result. Additionally, at the same time in order to overcome the decrease in the heart rate owing to the vagus nerve stimulation, the stimulation is applied to the heart for making the patient's heart rate be in a tolerance range. The arrhythmia treatment equipment is constituted by means for continuously measuring an electrogram, means for detecting a characteristic of the aforesaid electrogram indicative of the tachycardia, means for initializing memories of a series of characteristics, means for supplying one or more electrical stimulations to a patient nerve system, and means for initializing a series of characteristics of the electrogram subsequent to the stimulation of the vagus nerve.

If an excessive stimulation of the vagus nerve is performed, there is a problem that side-effects such as an influence to the organs other than the heart become remarkable where, for example, dyspepsia and nausea owing to an excessive secretion of gastric acid, insulin, glucagons and the like or cough increase, pharyngitis, laryngismus, paresthesia, dyspnea and induction of an asthmatic attack for patients with a history of asthma patient will be induced, and if an enough stimulation of the vagus nerve is not performed conversely, there is a problem that enough effect cannot be obtained.

SUMMARY OF THE INVENTION

A purpose of the present invention is to propose a heart treatment equipment where physical exercise, mental stress and the like is detected by a sensor for either one of ventricle contractility an activity, respiration, blood and the like and a fatal arrhythmia is prevented by controlling a vagus nerve stimulation.

Additionally, another purpose of the present invention is to propose a heart treatment equipment where the vagus nerve stimulation is performed based on the condition of the heart activity such that an appropriate vagus nerve stimulation can be given.

In order to achieve the purpose of the present invention, a heart treatment equipment for treating a patient according to the present invention comprises a nerve, stimulator for generating a nerve stimulating signal for stimulating a vagus nerve; a sensor for sensing living body information of the patient; and a controller connected to the nerve stimulator and the sensor, wherein the controller controls the nerve stimulator in response to an output of the sensor.

Further, one exemplified embodiment of the heart treatment equipment according to the present invention comprises a nerve stimulator for generating a nerve stimulating signal for stimulating a vagus nerve; a heart stimulator for generating a heart stimulating pulse for stimulating the heart; a heart contraction detector for detecting a heart contraction; a sensor for sensing living body information; and a controller connected to the sensor and the nerve stimulator for controlling the parameter of the nerve stimulating signal.

Then, for an exemplified embodiment of the heart treatment equipment according to the present invention, it is desirable that the controlled parameter of the nerve stimulating signal is at least one of a period between pulses, a pulse width a number of pulses, a pulse current, a pulse voltage a delay time, a rest time and a repetitive number or is a multiple combination chosen from these, and additionally, it is desirable for the sensor that a sensor for detecting the ventricle contractility is used for detecting especially one of a QT interval, an intracardiac electrogram area, a pre-ejection period, a stroke volume, a ventricle pressure and the like.

Further, a heart treatment equipment according to the present invention comprises a nerve stimulator for generating a nerve stimulating signal for stimulating a vagus nerve; a heart abnormal detector for detecting an abnormal condition of the heart; and a controller for connecting the nerve stimulator and the heart abnormal detector, wherein the controller controls the nerve stimulator in response to an output of the heart abnormal detector.

Further, a heart treatment equipment according the present invention is characterized by comprising a nerve stimulator for generating a nerve stimulating signal which stimulates the vagus nerve; waveform characteristic defining means for controlling the characteristic of the stimulation waveform which the nerve stimulator generates; a heart event detector for detecting a heart spontaneous event; a risk event detector connected to the heart event detector for detecting a risk event; and a controller for maintaining the relation between the type of the risk event and the waveform characteristic of the nerve stimulation and for setting a stimulation waveform characteristic corresponding to the detected tachycardia risk event into the waveform characteristic defining means based on the relation.

Here, the increase of the parasympathetic tone which is exerted by an electrical stimulation of the vagus nerve becomes different depending on the stimulation waveform. According to a heart treatment equipment of the present invention, when a high risk event which includes a ventricle tachycardia or a ventricle fibrillation is detected, a stimulation waveform which produces a strong parasympathetic tone is applied while a stimulations waveform which produces a weak parasympathetic-tone is applied when merely a decrease of the heart rate is aimed as in a usual case, so that an appropriate nerve stimulation can be performed according to the situation.

Furthermore, the present invention can be applicable not only to a heart treatment equipment but also to a heart treating method. According to the present invention the heart treating method comprises process for sensing living body information; and process for stimulating a vagus nerve in accordance with a variable parameter suitable for the living body information in response to the sensed living body information. The living body information is obtained by sensing information of a heart, information of a signal relied upon an autonomic nerve activity and the like.

In this heart treating method, it is also desirable that the parameter is at least one of a period between pulses, a pulse width, a number of pulses, a pulse current, a pulse voltage, a delay time, a rest time and a repetitive number or is a multiple combination chosen from these.

BRIEF DESCRIPTION OF THE DRAWINGS

FIG. 14 is a constitutional diagram of a ventricle pre-ejection period sensor used in the seventh exemplified embodiment of a heart treatment equipment according to the present invention;

FIG. 15 is a constitutional diagram of a stroke volume sensor used in the eighth exemplified embodiment of a heart treatment equipment according to the present invention;

DESCRIPTION OF THE PREFERRED EMBODIMENTS

Figure 1:
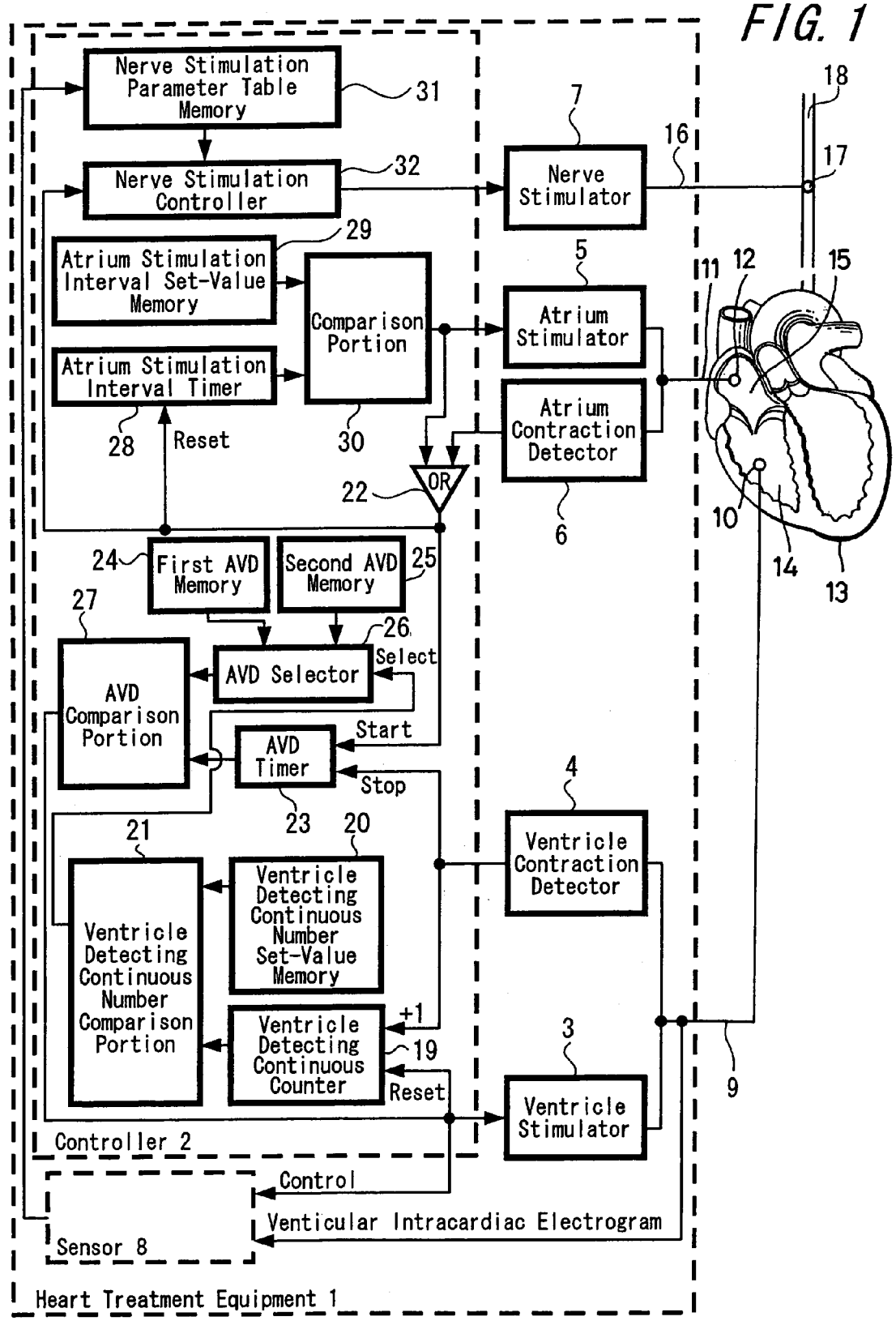
FIG. 1 is a block diagram showing constitutional examples of a first and a second exemplified embodiments of a heart treatment equipment according to the present invention.

A first exemplified embodiment of a heart treatment equipment according to the present invention will be described hereinafter in detail with reference to FIG. 1. It should be noted that "event" of a heart in this specification includes a contraction phenomenon which occurs in the heart (the atrium and/or the ventricle) regardless of a stimulation originated or a spontaneous occurrence.

The heart treatment equipment 1 is constituted by a controller 2, a ventricle stimulator 3 generating a right ventricle stimulating pulse for stimulating a right ventricle 14 of a heart 13, a ventricle contraction detector 4 detecting a spontaneous contraction of the right ventricle 14, an atrium stimulator 5 generating a right atrium stimulating pulse for stimulating a right atrium 15 of the heart 13, an atrium contraction detector 6 detecting a spontaneous contraction of the right atrium 15, a nerve stimulator 7 generating a nerve stimulating pulse for stimulating a vagus nerve 18, and a sensor 8.

The ventricle stimulator 3 and the ventricle contraction detector 4 are connected to a ventricle stimulating/detecting electrode 10 by means of a common ventricle 9, and the atrium stimulator 5 and the atrium contraction detector 6 are similarly connected to a atrium stimulating/detecting electrode 12 through an atrium lead 11. The ventricle stimulating/detecting electrode 10 and the atrium stimulating/detecting electrode 12 are arranged in the right ventricle 14 and the right atrium 15 of the heart 13 respectively.

Figure 2:
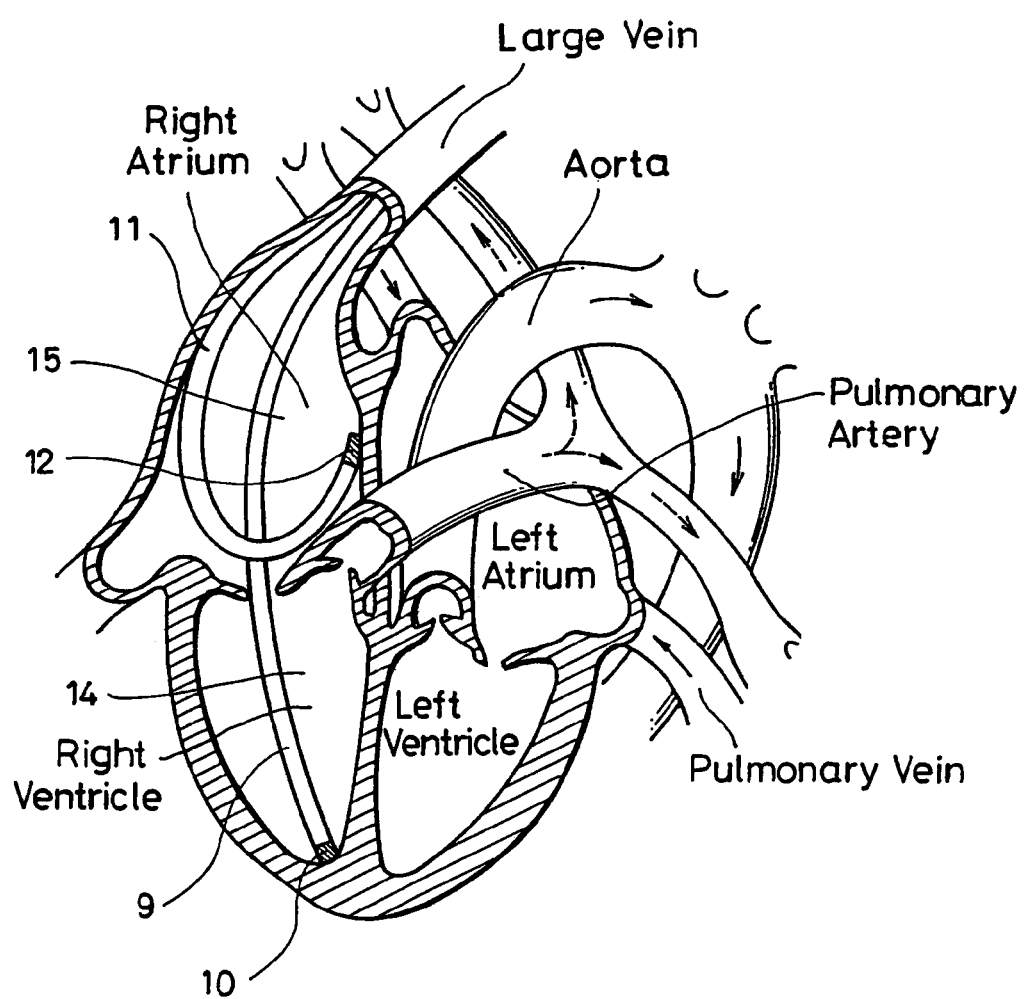
FIG. 2 is a layout diagram of stimulating/detecting electrodes which are used for a heart treatment equipment according to the present invention.

Generally, as an electrode for a heart, there is an epicardium electrode embedded in a cardiac muscle and a catheter electrode which is an electrode inserted into the heart through a large vein. FIG. 2 shows an example of catheter electrodes where all of the ventricle lead 9 and the atrium lead 11 are introduced to the right atrium 15 of the heart 13 firstly through a large vein. The atrium lead 11 which is inserted to the right atrium 15 through the large vein is inserted such as being hooked at its bended tip portion of J-shape in a right auricular appendage which protruded from the wall of the right atrium 15 and has a pouched form and the atrium stimulating/detecting electrode 12 is arranged such as being contacted with the inner wall of the right auricular appendage. Additionally, the ventricle lead 9 which is similarly inserted to the right atrium 15 through the large vein enters the right ventricle 14 through an atrioventricular valve and the ventricle stimulating/detecting electrode 10 which is provided at the tip portion of the ventricle lead 9 is arranged such as being contacted with an apex of the right ventricle 14.

Though it is not shown in FIG. 2, the nerve stimulator 7 is connected to a nerve stimulating electrode 17 by means of a nerve lead 16 and the nerve stimulating electrode 17 is fixed to a vagus nerve 18 by wrapping the latter. The region where the nerve stimulating electrode 17 is wrapped is preferably selected to be in a cervical region or at a right center position of the external carotid artery. Further, it is also possible to arrange the nerve stimulating electrode 17 so as to stimulate the vagus nerve 18 adjacent to a blood vessel wall by detaining a catheter electrode in the blood vessel. It is preferable to select the arrangement region in a subclavian vein.

The controller 2 of the heart treatment equipment 1 shown in FIG. 1 is constituted by a ventricle detecting continuous counter 19 connected to the ventricle stimulator 3 and a ventricle contraction detector 4, a ventricle detecting continuous number set-value memory 20, a ventricle detecting-continuous number comparison portion 21 supplied with outputs of the ventricle detecting continuous counter 19 and the ventricle detecting continuous number set-value memory 20, an OR circuit 22 supplied with an output of the atrium contraction detector 6 and an input to the atrium stimulator 5, atrioventricular delay (AVD) timer 23 supplied with an output of the OR circuit 22 and an output of the ventricle contraction detector 4, a first AVD memory 24 for storing a first AVD set-value which is an atrioventricular delay time at the time of normal, a second AVD memory 25 for storing a second. AVD set-value which is shorter than the atrioventricular delay time at the time of normal, an AVD selector 26 for selecting either one of the first AVD memory 24 and the second AVD memory 25, an AVD comparison portion 27 for detecting that the time measured by the AVD timer 23 becomes in conformity to the set-value selected by the AVD selector 26, an atrium stimulation interval timer 28 supplied with the output of the OR circuit 22, an atrium stimulation interval set-value memory 29, a comparison portion 30 for generating an output when the measured value of the atrium stimulation interval timer 28 become in conformity to the set-value stored in the atrium stimulation interval set-value memory 29, a nerve stimulation parameter table memory 31 supplied with an output of the sensor 8, and a nerve stimulation controller 32 supplied with the output of the OR circuit 22 for controlling a timing of the nerve stimulation.

Figure 3:
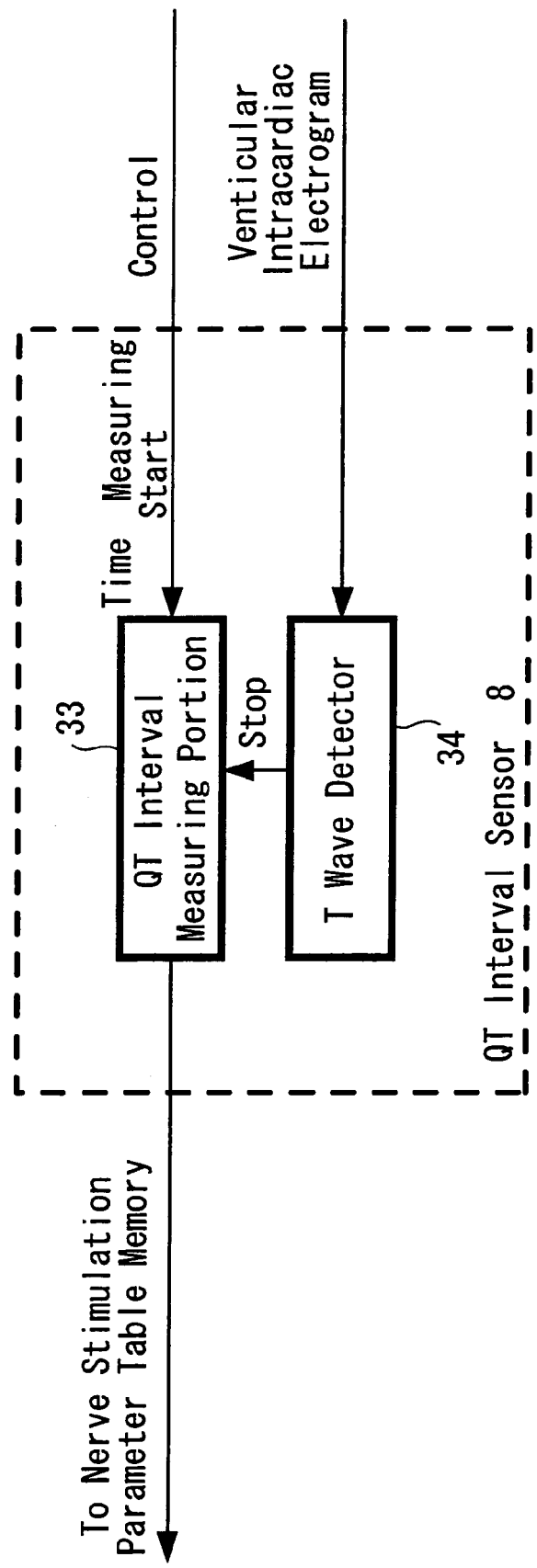
FIG. 3 is a constitutional diagram of a sensor for detecting a QT interval in the first exemplified embodiment of a heart treatment equipment according to the present invention.

FIG. 3 shows a QT interval sensor which is one of embodied examples of the sensor 8. This sensor 8 is constituted by a QT interval measuring portion 33 supplied with an output of the AVD comparison portion 27 of the controller 2 shown in FIG. 1 and a T wave detector 34 for detecting a T wave from an intraventicular electrogram is supplied from the ventricle detecting electrode 10 only when the ventricle stimulation is performed. The output of this T wave detector 34 is supplied to the QT interval measuring portion 33 and the QT interval is measured so as to be supplied to the nerve stimulation parameter table memory 31 of the controller 2 shown in FIG. 1.

Here, it will be described about the QT interval measuring using the intraventicular electrogram shown in FIG. 4. This intraventicular electrogram is a little bit different from a usual one which is measured by putting an electrode on the body surface. More specifically, in the intraventicular electrogram, a P wave for observing a contraction of the atrium hardly exists and the intraventicular electrogram is constituted by a QRS complex which starts from the stimulation of the ventricle and T wave having a different polarity from the QRS complex. The T wave is a wave which is emanated when the ventricle contraction is loosened, that is, when the ventricles are repolarized.

As already explained, the QT interval is a time after a time point when the right ventricle 14 is stimulated until the ventricles are repolarized. When the QT interval is measured by using the intraventicular electrogram, time differentiation of the T wave is conducted and the QT interval is measured by setting a T point which is a point when the differentiated value (slope) becomes a negative maximum value. This QT interval is living body information relating to a representative ventricle contractility and is around 400 ms on a usual condition, that is, at the time of normal, but the QT interval becomes shorter less than a half at the time of normal when the sympathetic tone is high in case of an intense physical exercise or mental stress.

The first exemplified embodiment of a heart treatment equipment according to the present invention is one where the sensor 8 of FIG. 1 is constituted by the QT interval sensor of FIG. 3.

First, when a contraction of the right atrium 15 is detected by the atrium contraction detector 6, the atrium contraction detector 6 transmits its output to the atrium stimulation interval timer 28 and the AVD timer 23 through the OR circuit 22 such that the atrium stimulation interval timer 28 is made reset and at the same time the counting operation of the AVD timer 23 is made started.

In an initial condition, the AVD selector 26 selects an atrioventricular delay time set-value at the time of normal, for example, 150 ms which is stored in the first AVD memory 24. In a normal heart, a spontaneous ventricle contraction occurs before counting the set-value stored in the first AVD memory 24 after the AVD timer 23 starts, so that the AVD timer 23 is stopped every at that time by the output of the ventricle contraction detector 4. Consequently, the AVD timer 23 will not be counted up to the set-value stored in the first AVD memory 24 which is set in the AVD selector 26. Therefore, in this case, an output cannot be obtained from the AVD comparison portion 27 and the ventricle stimulator 3 is not supplied with an output of the AVD comparison portion 27, so that a forced ventricle stimulation is not performed.

If it is a case that a spontaneous ventricle contraction does not occur within the atrioventricular delay time at the time of normal which is stored in the first AVD memory 24, an output cannot be obtained from the ventricle contraction detector 4, so that the AVD timer 23 does not stop and continues counting. More specifically, the AVD timer 23 continues counting until it becomes in conformity to the set-value stored in the first AVD memory 24 which is selected by the AVD selector 26 and generates an output from the AVD comparison portion 27 at the time point in conformity thereto.

The output of the AVD comparison portion 27 is transmitted to the ventricle stimulator 3 and the stimulation of the right ventricle 14 is performed by the ventricle stimulating electrode 10 through the ventricle lead 9. At the same time, it is added to the ventricle detecting continuous counter 19 and resets the ventricle detecting continuous counter 19. Additionally, the output of the AVD comparison portion 27 is supplied to the QT interval measuring portion 33 of the sensor 8 shown in FIG. 3 and the QT interval measuring portion 33 is made to start.

The ventricle detecting continuous counter 19 which is reset by the ventricle stimulation (output of the AVD comparison portion 27) is increment every time when an spontaneous ventricle contraction is detected by the ventricle contraction detector 4 and an output is generated from the ventricle detecting continuous number comparison portion 21 when the ventricle contraction is continuously detected until the number of times (specifically, around 3 to 10 times) which is stored in the ventricle detecting continuous number set-value memory 20. The output of this ventricle detecting continuous number comparison portion 21 is supplied to the AVD selector 26. The AVD selector 26 changes its set-value from the set-value of the first AVD memory 24 to the set-value of the second AVD memory 25 in response to the output of the ventricle detecting continuous number comparison portion 21.

The set-value stored in this second AVD memory 25 is selected shorter than about 150 ms which is the atrioventricular delay time at the time of normal and, for example, is selected to be 100 ms. Here, when it is assumed that set-value is 100 ms of the atrioventricular delay time, the ventricle contraction is not detected by the ventricle contraction detector 4 during when the AVD timer 23 counts 100 ms, so that the AVD timer 23 always counts the set-value stored in the second AVD memory 25 such that an output is obtained from the AVD comparison portion 27 every time.

The output of this AVD comparison portion 27 is added to the ventricle stimulator 3, the ventricle detecting continuous counter 19 and the sensor 8 (QT interval measuring portion 33 of FIG. 3). In this way, the measurement of the QT interval as living body information which expresses the degree of excitement of the sympathetic nerve is conducted.

More specifically, the QT interval is measured by switching the atrioventricular delay time set-value in the AVD selector 26 from the first AVD memory 24 to the second AVD memory 25 so as to perform the forced ventricle stimulation.

The T wave detector 34 in the sensor 8 shown in FIG. 3 is designed such that the T wave is detected only when the right ventricle 14 is stimulated, so that when the T wave is detected, an output thereof is transmitted to the QT interval measuring portion 33 and the counting operation of the QT interval measuring portion 33 stops. Then, the measured QT interval is transmitted from the QT interval measuring portion 33 to the nerve stimulation parameter table memory 31 of the controller 2 and a parameter in response to the measured QT interval is selected.

Figure 18:
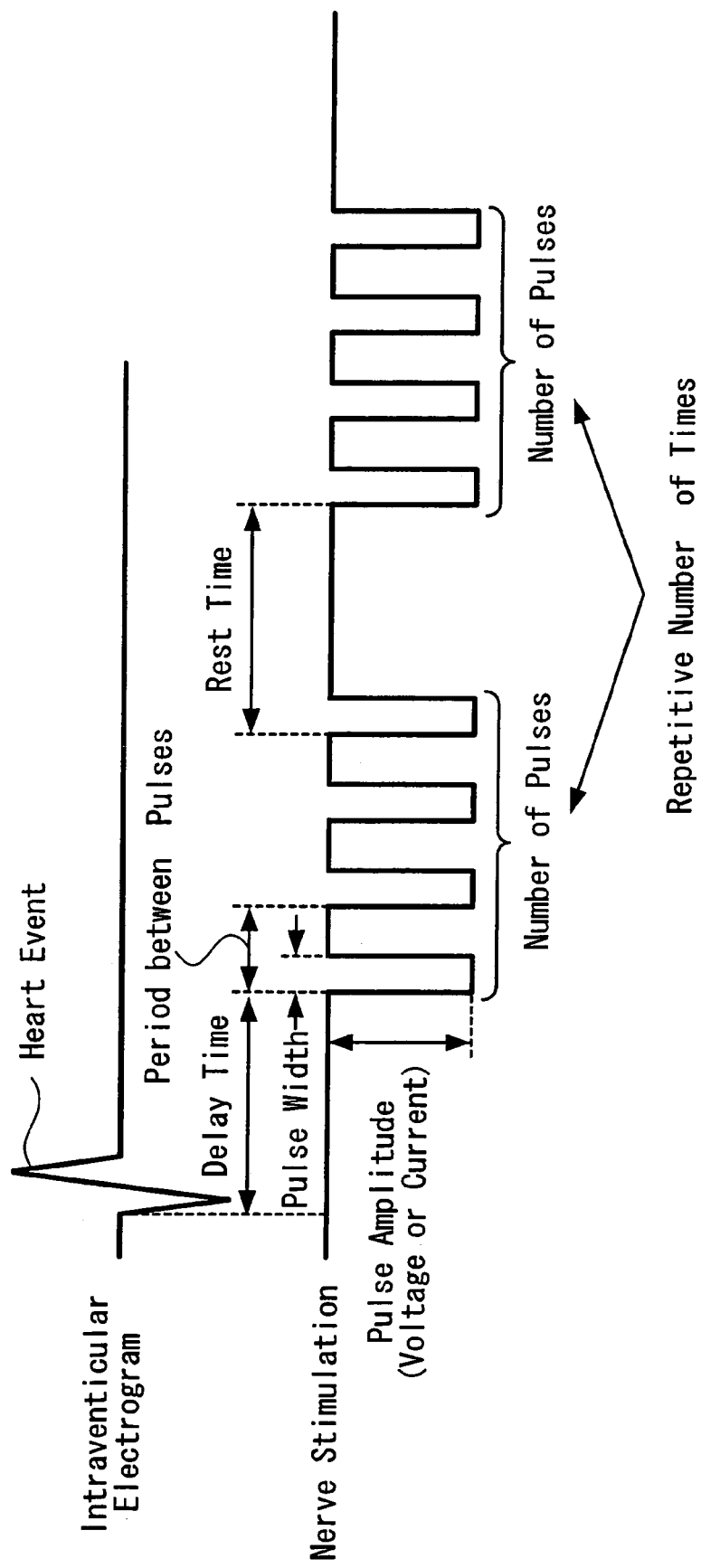
FIG. 18 is a diagram explaining a nerve stimulation waveform parameter.

As to a parameter selected in response to this QT interval, it can be picked up from such as a number of pulses in a nerve stimulating pulse train, a delay time after the atrium event until the vagus nerve 18 is stimulated, an amplitude of the nerve stimulating pulse, a pulse width of the nerve stimulating pulse, a period between pulses of the nerve stimulating pulses, a number (repetitive number of times) of the nerve stimulating pulse train, the time (pause time) between the nerve stimulating pulse trains and an on/off (nerve stimulation flag) of the nerve stimulation, but it should be noted that it is possible to perform the stimulation of the vagus nerve 18 by compounding such parameters in response to the situation of the patient. FIG. 18 is a diagram for explaining aforesaid nerve stimulation parameters where they are shown in contrast to a heart event in an electrocardiogram.

Some of the controlling examples of the nerve stimulation parameter are shown in table 1 to table 3. When the QT interval is in a normal range (less than or equal to QTnormal×0.9), the stimulation of the vagus nerve 18 is not performed in either of the controlling examples by setting the nerve stimulation flag off, but when the QT interval becomes shorter than a normal range (more than QTnormal× 0.9), the vagus nerve 18 stimulation is performed by setting the nerve stimulation flag on and by controlling the nerve stimulation parameter in response to the degree of the shortage. Table 1 is an example where the number of pulses for performing the nerve stimulation is controlled in response to the QT interval and the number of pulses of the nerve stimulating pulses is increased in proportion to the degree of the shortage of the QT interval compared with the QT interval of normal. Table 2 is an example where the period between pulses is controlled in response to the QT interval. More specifically, the stimulation frequency is increased by making the pulse period between the nerve stimulating pulses shorter in proportion to the degree of the shortage of the QT interval compared with the QT interval of normal. Table 3 is an example where the delay time after the atrium event until the nerve stimulation is changed in response to the QT interval and the timing for performing the nerve stimulation after the atrium event is delayed in proportion to the degree of the shortage of the QT interval compared with the QT interval of normal.

TABLE 1

Relation between QT interval and nerve stimulation waveform (Control of Number of Pulses)

| | Nerve Stimulation Waveform Characteristic | | | | | | | |
|---|---|---|---|---|---|---|---|---|
| QT interval | Number of Pulses | Delay Time | Amplitude | Pulse Width | Period between Pulses | Repetitive Number of Times | Pause Time | Nerve Stimulation Flag |
| ~0.9 × QTnormal | — | — | — | — | — | — | — | off |
| 0.9 × QTnormal~ | 1 | 0 msec | 3 V | 1 msec | — | 1 | — | on |
| 0.8 × QTnormal~ | 2 | 0 msec | 3 V | 1 msec | 50 msec | 1 | — | on |
| 0.7 × QTnormal~ | 3 | 0 msec | 3 V | 1 msec | 50 msec | 1 | — | on |
| 0.6 × QTnormal~ | 4 | 0 msec | 3 V | 1 msec | 50 msec | 1 | — | on |

Qtnormal = ~400 msec

TABLE 2

Relation between QT interval and nerve stimulation waveform (Control of Period between Pulses)

| QT interval | Nerve Stimulation Waveform Characteristic | | | | | | | |
|---|---|---|---|---|---|---|---|---|
| | Number of Pulses | Delay Time | Amplitude | Pulse Width | Period between Pulses | Repetitive Number of Times | Pause Time | Nerve Stimulation Flag |
| ~0.9 × QTnormal | — | — | — | — | — | — | — | off |
| 0.9 × QTnormal~ | 2 | 0 msec | 3 V | 1 msec | 50 msec | 1 | — | on |
| 0.8 × QTnormal~ | 2 | 0 msec | 3 V | 1 msec | 40 msec | 1 | — | on |
| 0.7 × QTnormal~ | 2 | 0 msec | 3 V | 1 msec | 30 msec | 1 | — | on |
| 0.6 × QTnormal~ | 2 | 0 msec | 3 V | 1 msec | 25 msec | 1 | — | on |

Qtnormal = ~400 msec

TABLE 3

Relation between QT interval and nerve stimulation waveform (Control of Delay Time)

| QT interval | Nerve Stimulation Waveform Characteristic | | | | | | | |
|---|---|---|---|---|---|---|---|---|
| | Number of Pulses | Delay Time | Amplitude | Pulse Width | Period between Pulses | Repetitive Number of Times | Pause Time | Nerve Stimulation Flag |
| ~0.9 × QTnormal | — | — | — | — | — | — | — | off |
| 0.9 × QTnormal~ | 2 | 0 msec | 3 V | 1 msec | 50 msec | 1 | — | on |
| 0.8 × QTnormal~ | 2 | 5 msec | 3 V | 1 msec | 50 msec | 1 | — | on |
| 0.7 × QTnormal~ | 2 | 10 msec | 3 V | 1 msec | 50 msec | 1 | — | on |
| 0.6 × QTnormal~ | 2 | 15 msec | 3 V | 1 msec | 50 msec | 1 | — | on |

Qtnormal = ~400 msec

The nerve stimulation parameter table memory 31 memorizes tables relating to nerve stimulation parameters as shown in the table 1 to the table 3 and based on the QT interval measured by the QT interval measuring portion 33 of FIG. 3, it selects whether or not the nerve stimulation is performed and when performed, determines parameters and then transmits them to the nerve stimulation controller 32.

When the atrium contraction detector 6 detects a contraction of the right atrium 15 under a condition that the nerve stimulation flag is on in the nerve stimulation controller 32, the atrium stimulation interval timer 28 is made reset by output of the atrium contraction detector 6 through the OR circuit 22. Time corresponding to a cardiac cycle duration at the time of normal is set in the atrium stimulation interval set-value memory 29 and if the atrium contraction is not detected within that time, the measured value of the atrium stimulation interval timer 28 reaches the set-value stored in the atrium stimulation interval set-value memory 29 and the comparison portion 30 emanates an output. An atrium stimulation is performed by the output of the comparison portion 30 and at the same time the output of the comparison portion 30 is supplied to the nerve stimulation controller 32 through the OR circuit 22. The nerve stimulation controlled 32 transmits a signal to the nerve stimulator 7 based on the control of various parameters in response to the QT interval shown from the table 1 to table 3 and selected by the nerve stimulation parameter table memory 31 such that the vagus nerve 18 is stimulated by means of the nerve lead 16 and the nerve stimulating electrode 17. It should be noted that it is needless to say that parameters shown from the table 1 to table 3 are not only used individually but also used in combination with some others according to the condition of the patient.

In this way, the condition of the physical exercise or the mental stress of the patient is detected by the QT interval and it is controlled such that when the intensity of the physical exercise or the mental stress is high, a relatively strong nerve stimulation is performed and when it is low, a relatively weak nerve stimulation is performed or no nerve stimulation is performed.

Figure 5:
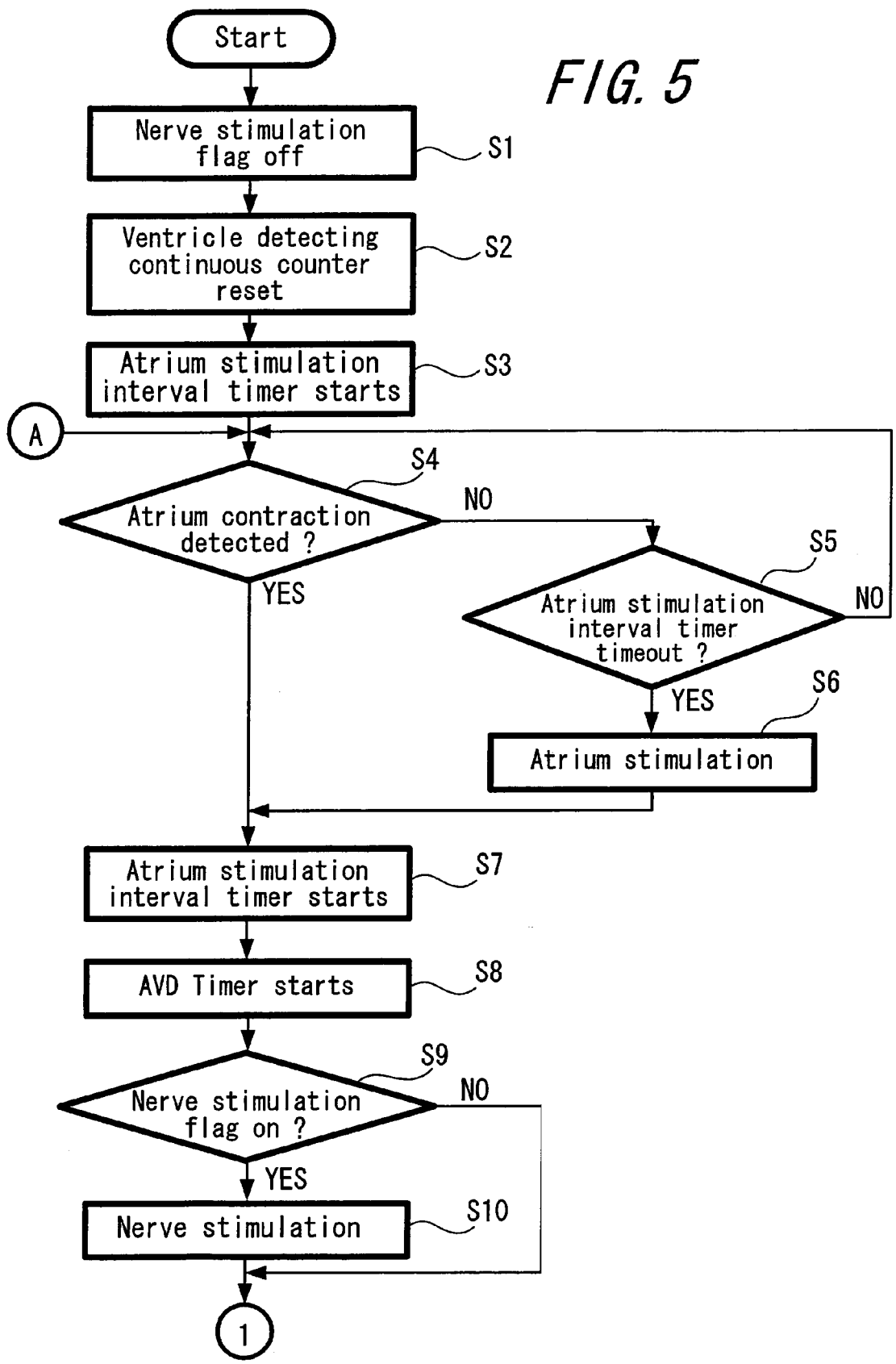
FIG. 5 is a flowchart showing an operation of the first exemplified embodiment of a heart treatment equipment according to the present invention where QT interval measuring sensor is used as the sensor in the block diagram shown in FIG. 1.
Figure 5:
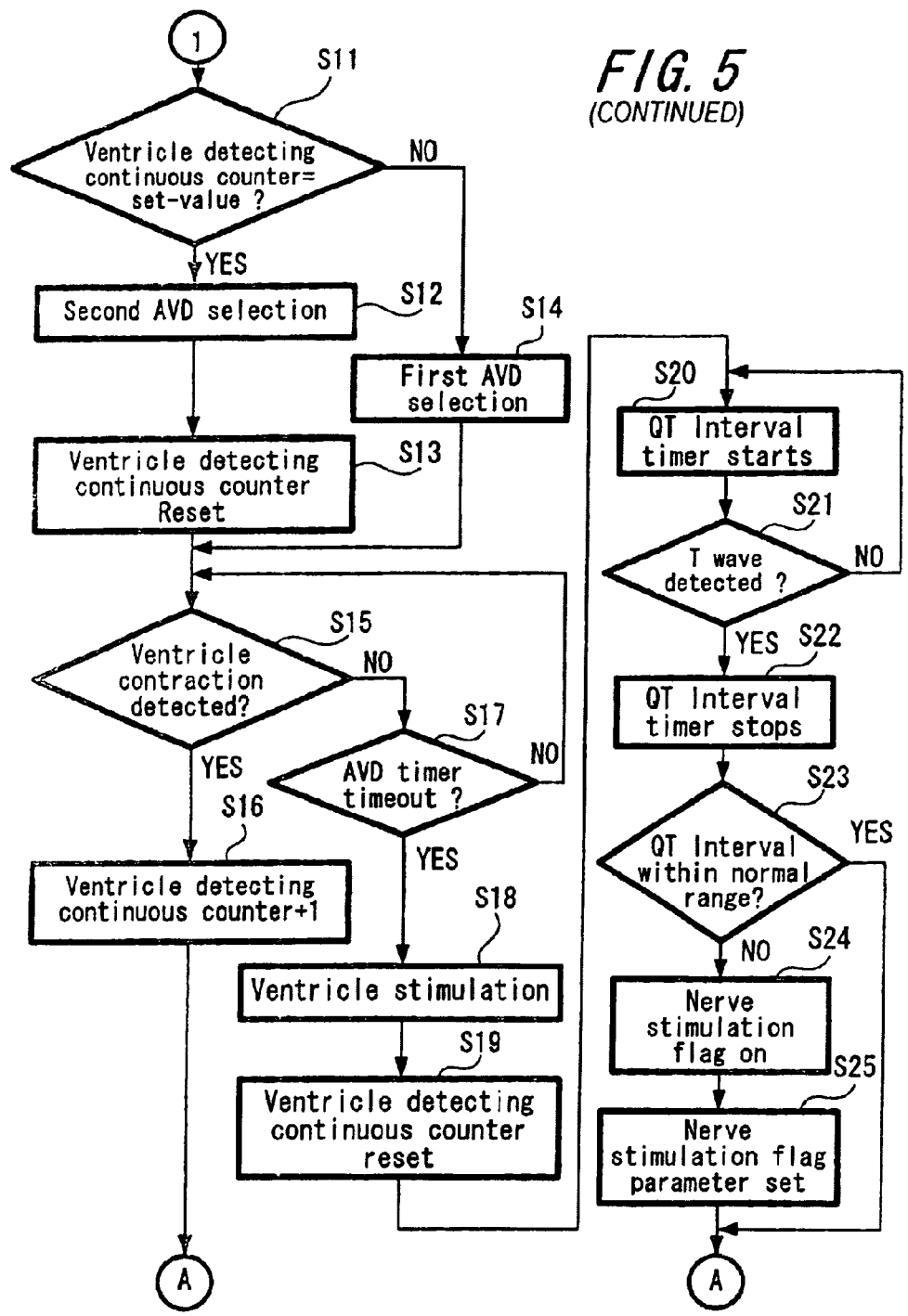

FIG. 5 is a flowchart for explaining the operation of the first ⑦exemplified embodiment according to the present invention.

The operation of the first exemplified embodiment is explained in detail using the flowchart of FIG. 5 hereinafter. First, the nerve stimulation flag of the nerve stimulation controller 32 is made off (step S1). Next, the ventricle detecting continuous counter 19 is made reset (step S2) and further, the atrium stimulation interval timer 28 is made reset (step S3) so as to complete the initialization of the whole system.

Next, it is judged in the atrium contraction detector 6 whether or not the atrium contraction is detected (step S4). If the atrium contraction is not detected in the judgment step S4, it is judged whether or not the atrium stimulation interval timer 28 times out, that is, whether or not the measured time of the atrium stimulation interval timer 28 exceeds the set value stored in the atrium stimulation interval set-value memory 29 (step S5) and when it is judged the atrium stimulation interval timer 28 times out, an out put is emanated from the comparison portion 30 to the atrium stimulator 5 and the atrium stimulation is performed (step S6). When it is judged in the judgment step S5 that the atrium stimulation interval timer 28 does not time out, it will wait again for the detection of the atrium contraction. When the atrium contraction is detected in the judgment step S4, the atrium stimulation interval timer 28 is made reset and starts the time measuring again (step S7) and at the same time the time measuring operation of the AVD timer 23 is made to start (step S8).

Next, it is judged whether or not the nerve stimulation flag of the nerve stimulation controller 32 is made on (step S9) and if the nerve stimulation flag is on, a signal is emanated from the nerve stimulation controller 32 to the nerve stimulator 7 and the stimulation of the vagus nerve 18 is performed (step S10). When it is judged in the judgment step S9 that the nerve stimulation flag is off, the nerve stimulation is not performed and the flow proceeds to the next step.

When the ventricle contraction detector 4 detects the ventricle contraction, it increments the ventricle detecting continuous counter 19 and it is judged whether or not the counting value of the ventricle detecting continuous counter 19 reaches the set-value stored in the ventricle detecting continuous number set-value memory 20, that is, whether or not the ventricle contraction was detected continuously as many as 3 to 10 times which are stored in the ventricle detecting continuous number set-value memory 20 (step S11). In a case when the counting value of the ventricle detecting continuous counter 19 reaches aforesaid set-value, an output is given from the ventricle detecting continuous number comparison portion 21 to the AVD selector 26 and the AVD selector 26 selects the set-value stored in the second AVD memory 25 (step S12). As the set-value of the atrioventricular delay time stored in the second AVD memory 25 is selected shorter than a usual value, the AVD timer 23 reaches the set-value of aforesaid second AVD memory 25 before the ventricle contraction detector 4 detects a spontaneous ventricle contraction, so that an output is obtained from the AVD comparison portion 27 and a forced ventricle stimulation is performed and at the same time the ventricle detecting continuous counter 19 is made reset (step S13).

If it is judged in the judgment step S11 that the ventricle detecting continuous counter 19 does not reach the set-value stored in the ventricle detecting continuous number set-value memory 20, an output cannot be obtained from the ventricle detecting continuous number comparison portion 21 to the AVD selector 26, so that the AVD selector 26 keeps the situation of selecting the set-value stored in the first AVD memory 24 (step S14).

Subsequently, it is judged in the ventricle contraction detector 4 whether or not the ventricle contraction is detected (step S15) and if the ventricle contraction is detected, the ventricle detecting continuous counter 19 is made incremented (step S16). When it is judged in the judgment step S15 that the ventricle contraction is not detected, it is judged whether or not the AVD timer 23 is timeout, that is, whether or not the measured time of the AVD timer 23 exceeds the set-value of the first AVD memory 24 or the second AVD memory 25 which is selected by the AVD selector 26 (step S17).

If it is judged in the judgment step S17 that the AVD timer 23 does not time out, it again waits for the detection of the ventricle contraction, but if the AVD timer 23 times out, an output is emanated from the AVD comparison portion 27 and the ventricle stimulation is performed by a the ventricle stimulator 3 (step S18) while at the same time the ventricle detecting continuous counter 19 is made reset (step S19) and further, the counting operation of the QT interval measuring portion 33 is made to start (step S20).

In this situation, the intraventicular electrogram is differentiated within a predetermined period corresponding to the T wave portion in the T wave detector 34 of the sensor 8 and a time point when the negative slope of the T wave becomes maximum is detected by that differentiated waveform (step S21) and the time measuring of the QT interval measuring portion 33 is stopped (step S22). When the negative maximum slope of the T wave is detected and the QT interval is measured, the measured QT interval is transmitted to the nerve stimulation parameter table memory 31 and compared with the QT interval (QTnormal) which becomes a standard value. As a result of the comparison, it is judged first whether or not the QT interval is within a normal range (step S23) and if it is within a normal range, the flow proceeds with the nerve stimulation flag being made off while if it is out of (shorter than) a normal range, the nerve stimulation flag is made on (step S24) and various parameters for the nerve stimulation are selected in response to the measured QT interval (step S25).

Figure 6:
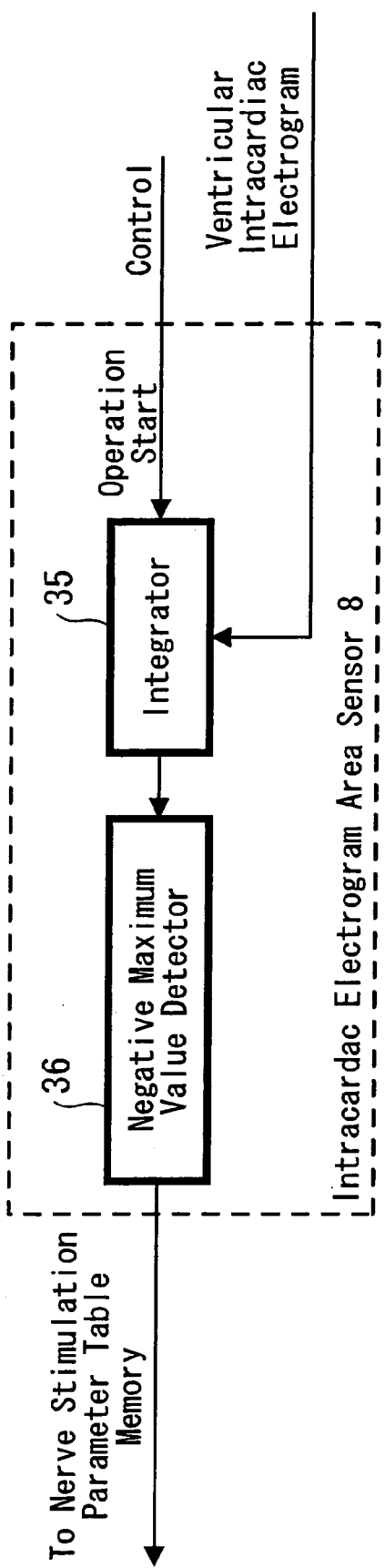
FIG. 6 is a constitutional diagram of an intraventicular electrogram area sensor for measuring an intraventicular electrogram area which is used in the second exemplified embodiment of a heart treatment equipment according to the present invention.

Next, an intraventicular electrogram area sensor 8 of another embodied example is shown in FIG. 6. The sensor 8 measures the area of the intraventicular electrogram so as to make it as living body information of a patient and is constituted by an integrator 35 supplied with the input to the ventricle stimulator 3 of FIG. 1, that is, supplied with the output of the AVD comparison portion 27 and intraventicular electrogram information and by a negative maximum value detector 36 for detecting the negative maximum value from the output of that integrator 35.

Figure 4A:
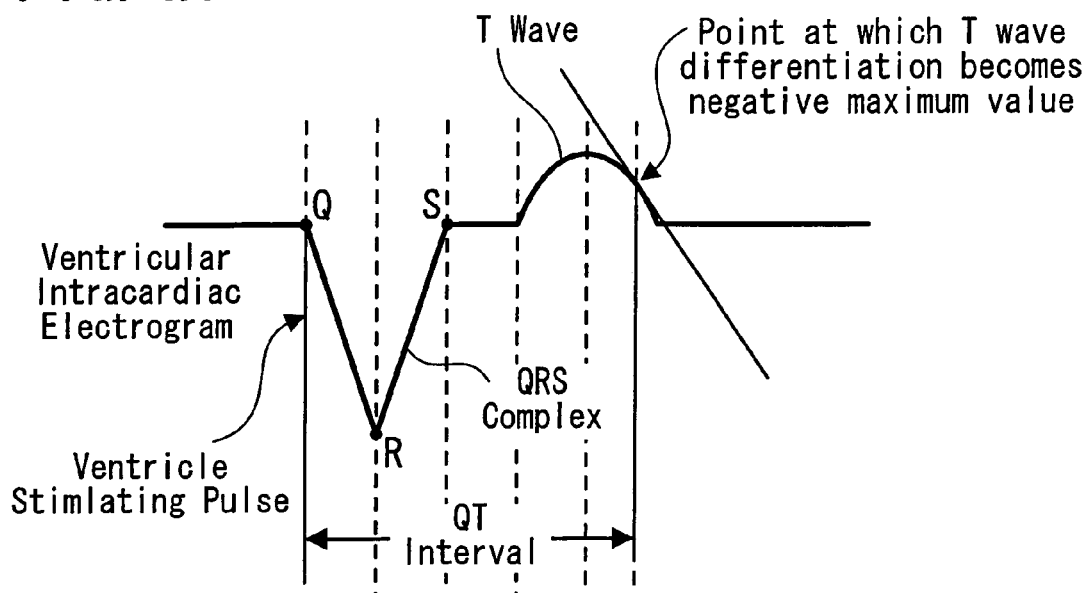
FIG. 4A is a waveform diagram showing an intraventicular electrogram and QT interval.
Figure 4B:
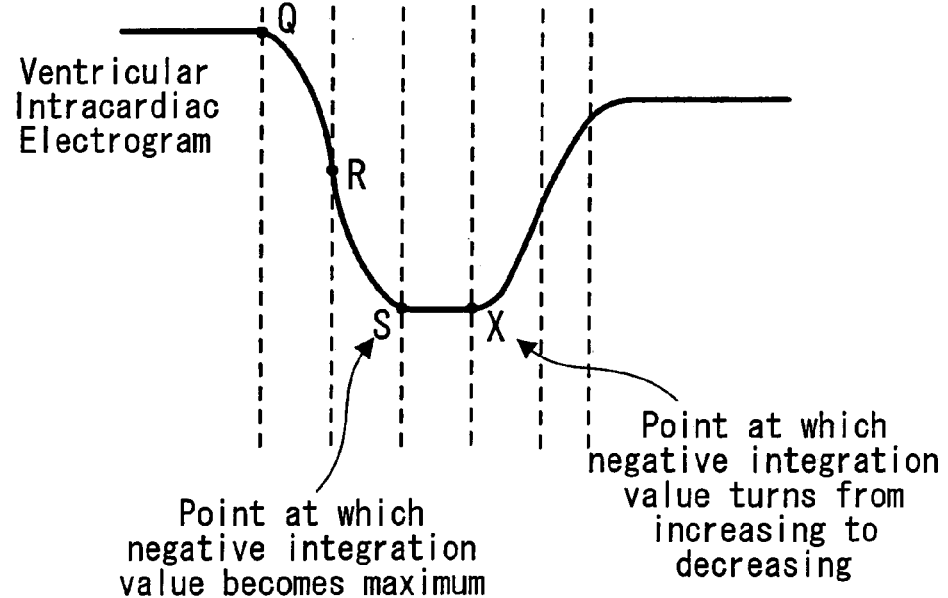
FIG. 4B is a waveform diagram obtained by integrating the intraventicular electrogram.

Similarly as the QT interval measuring, the integrator 35 starts the integration of the intraventicular electrogram which is shown in FIG. 4A and is transmitted when the ventricle stimulation is performed by the ventricle stimulator 3. The integrated waveform is shown in FIG. 4B. As clear by FIG. 4B, when the QRS complex (negative polarity) is integrated from a Q point where the ventricle stimulation is performed by the ventricle stimulator 3, the value of the negative area increases monotonously, but aforesaid negative integrated value turns to a decreasing direction at the stage of integrating the T wave, because the T wave has an opposite (positive) polarity with respect to the QRS complex. The intraventicular electrogram area has a negative maximum value corresponding toga value on a line from a point S when the integration of the QRS complex is finished to a time point (tentatively named as "X") when the detection of the T wave starts. The negative maximum value detector 36 detects aforesaid value and transmits this negative integrated maximum value to the nerve stimulation parameter table memory 31 as living body information. Then, various parameters are selected in the nerve stimulation parameter table memory 31 in response to the negative integrated maximum value. As to the nerve stimulation parameter, similarly as when the QT interval is concerned, it can be picked up from such as a number of pulses in a nerve stimulating pulse train, a delay time after the atrium event until the vagus nerve 18 is stimulated, an amplitude of the nerve stimulating pulse, a pulse width of the nerve stimulating pulse, a period between pulses of the nerve stimulating pulses, a number (repetitive number of times) of the nerve stimulating pulse train, the time (pause time) between the nerve stimulating pulse trains and an on/off (nerve stimulation flag) of the nerve stimulation.

Figure 7:
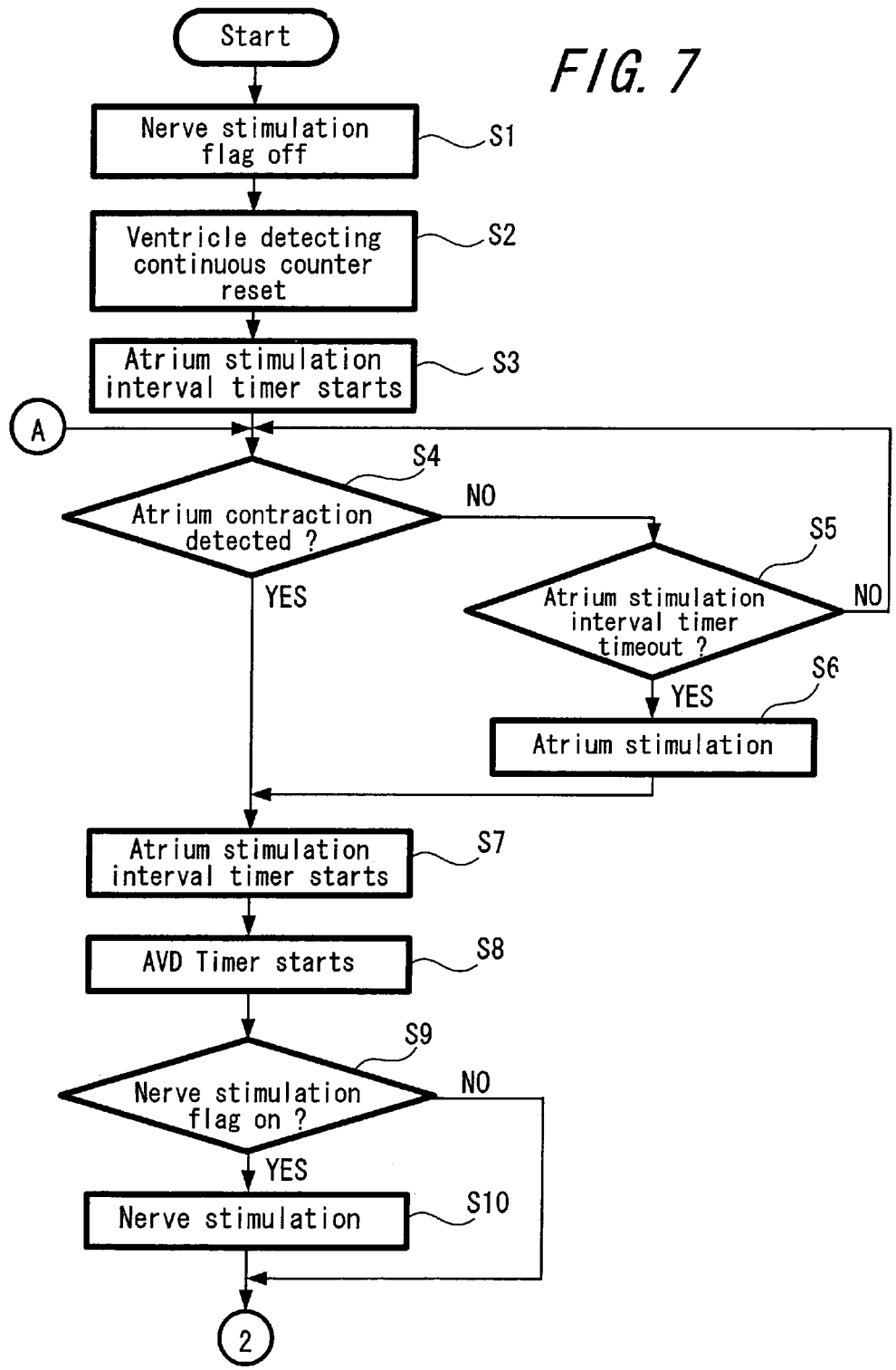
FIG. 7 is a flowchart showing an operation of the second exemplified embodiment of a heart treatment equipment according to the present invention where an intraventicular electrogram area sensor is used as the sensor of the block diagram shown in FIG. 1.
Figure 7:
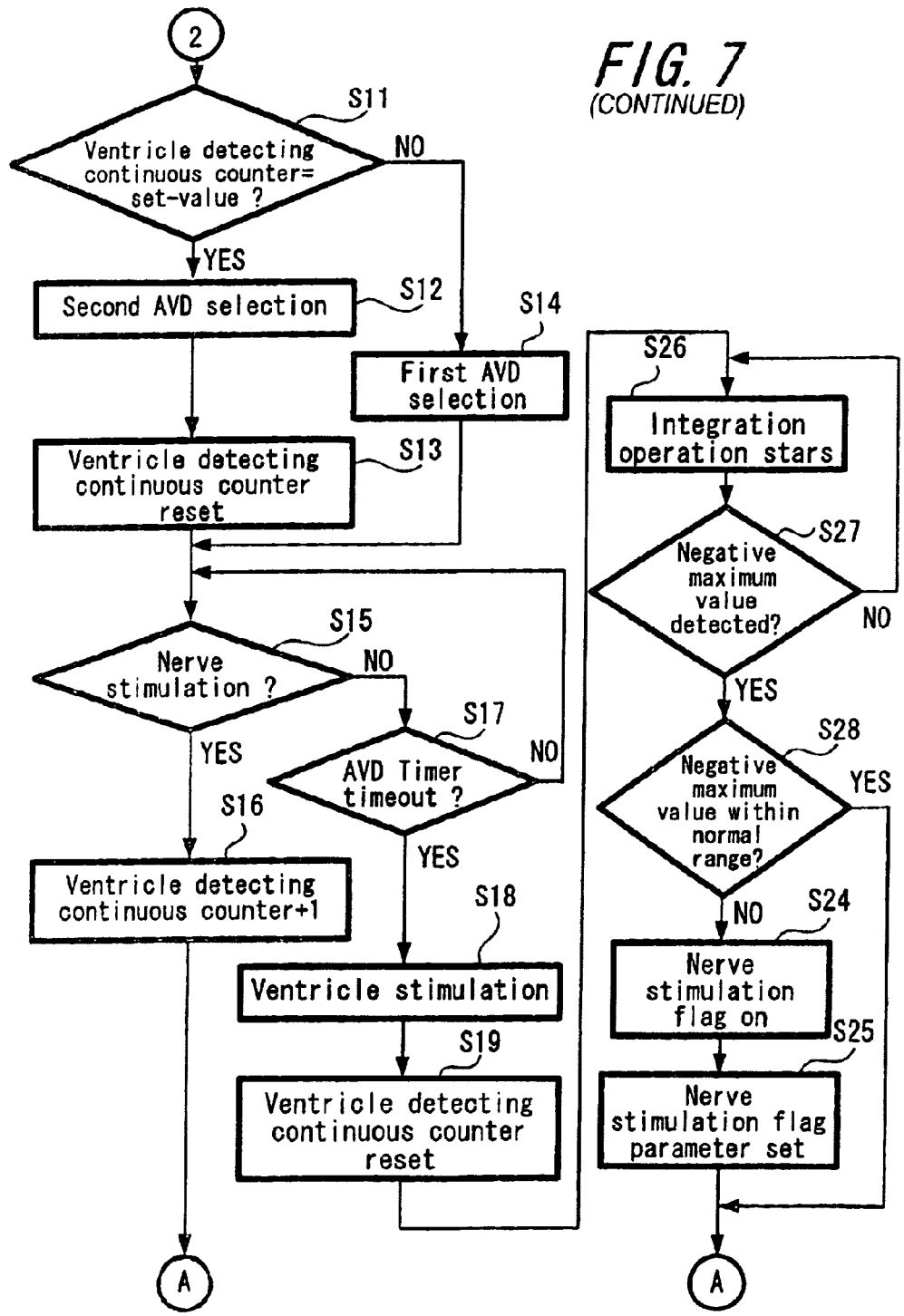

Next, the heart treatment equipment when an intraventicular electrogram area sensor is used as shown in FIG. 6 is named as a second exemplified embodiment according to the present invention and its operation will be described according to FIG. 7.

From step S1 to step S19 and from step S23 to step S25 are repetitions of those shown in FIG. 5, so that the explanation thereof will be omitted.

The explanation will be added from the stage of step S18 where the AVD timer 23 times out, an output is emanated from the AVD comparison portion 27 and the ventricle stimulation is performed by the ventricle stimulator 3. When the ventricle stimulation is performed, the ventricle detecting continuous counter 19 is made reset (step S19) and at the same time an integration operation of the intraventicular electrogram is made to start in the integrator 35 of the sensor 8 (step S26).

At this time, the QRS complex of the intraventicular electrogram is negative as shown in FIG. 4A, so that the result of the integration operation is detected as a negative signal output. Next, it is judged whether or not the negative maximum value was detected (step S27) and when it is judged that the negative maximum value was detected, it is judged first whether the negative maximum value is within a normal range (step S28), and when it is in a normal range, the flow proceeds with the nerve stimulation flag being maintained off while when it is out of the normal range, the nerve stimulation flag is made on (step S24) and various parameters for the nerve stimulation are selected in response to the measured negative maximum value (step S25).

Next, a third exemplified embodiment of a heart treatment equipment according to the present invention will be explained using a block diagram of FIG. 8. The same reference numerals are put on the corresponding portions to those of the block diagram shown in FIG. 1 and the explanation thereof will be done just simply. According to the third exemplified embodiment of the present invention, the constitution of the controller 2 and the constitution of the sensor 8 are different from those of the first and second exemplified embodiments which are formed by combining FIG. 1 and FIG. 3 and combining FIG. 1 and FIG. 6, so that the explanation will be done hereinafter centering around that point.

Figure 8:
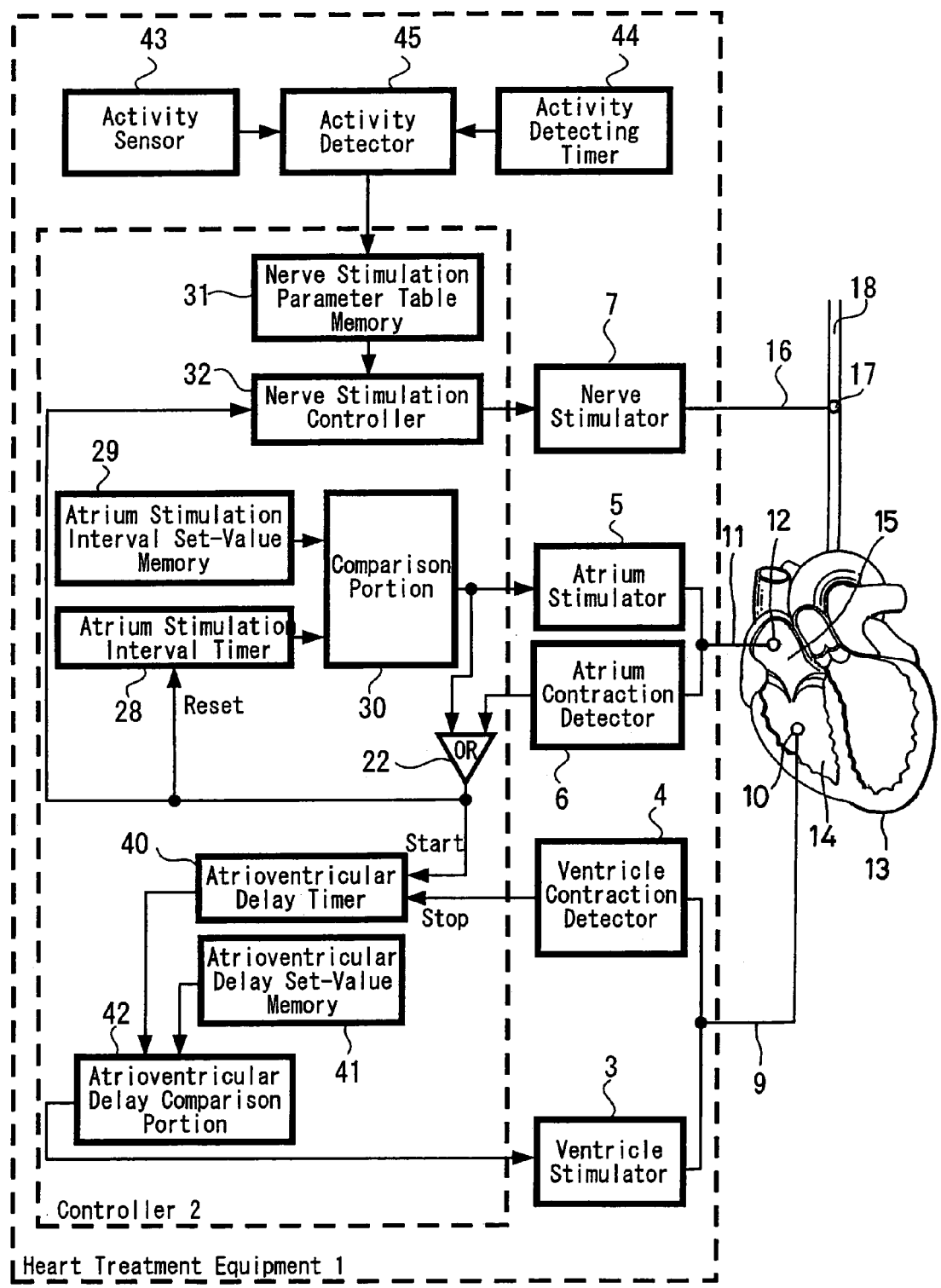
FIG. 8 is a block diagram showing a constitutional example a third exemplified embodiments of a heart treatment equipment according to the present invention.

In the third exemplified embodiment of the heart treatment equipment according to the present invention shown in FIG. 8, it is characterized in that an activity sensor 43 is provided instead of the sensor 8 of the first exemplified embodiment shown in FIG. 1. For the activity sensor 43, a piezoelectric sensor or an acceleration sensor is generally used. The sensor is arranged inside of a housing of the heart treatment equipment 1 which is implanted in a chest subcutaneously and it is mounted directly to the housing or on a circuit board thereof. In the piezoelectric sensor, the crystal thereof generates an electric signal when a stress is added to the piezoelectric crystal by means of a physical movement. The acceleration sensor is generally constituted so as to have a cantilever beam construction and the beam has a physical movement or displacement by acceleration such that an electric signal is generated. A patient motion is detected based on the repetition-rate, the strength or the strength within a certain frequency range with respect to this electric signal generated. When an intense physical exercise is conducted, the change (acceleration of vibration) of the activity increases and the sympathetic tone increase. Consequently, it becomes possible to measure the level of the sympathetic tone by detecting the acceleration or the vibration in the activity sensor 43. Then, an output of the activity sensor 43 is detected by an activity detector 45 at an appropriate time interval which was measured by a body motion detecting timer 44 such that an amount change of the physical exercise on each measurement is measured.

In the block diagram of FIG. 8, the controller 2 is constituted by the OR circuit 22 supplied with the input to the atrium stimulator 5 and the output from the atrium contraction detector 6, an atrioventricular delay timer 40 (same as the AVD timer 23 of FIG. 1) which start the time measuring by being supplied with the output of the OR circuit 22, an atrioventricular delay set-value memory 41 storing an atrioventricular delay time at the time of normal as a set-value, an atrioventricular delay comparison portion 42 for detecting that the time measured by the atrioventricular delay timer 40 becomes in conformity to the set-value stored in the atrioventricular delay set-value memory 41, the atrium stimulation interval timer 28 supplied with the output of the OR circuit 22, the atrium stimulation interval set-value memory 29, the comparison portion 30 which generates an output when the measured value of the atrium stimulation interval timer 28 becomes in conformity to the set-value stored in the atrium stimulation interval set-value memory 29, the nerve stimulation parameter table memory 31 supplied with an output from the activity detector 45 which detects the output from the activity sensor 43 at every appropriate time interval measured by the activity detecting timer 44, and the nerve stimulation controller 32 supplied with an output of the OR circuit 22 and for controlling the timing of the nerve stimulation.

The operation of the third exemplified embodiment of the heart treatment equipment according to present invention will be described hereinafter.

In FIG. 8, when the atrium contraction detector 6 detects a contraction of the right atrium 15, the atrium contraction detector 6 transmits its output to the atrium stimulation interval timer 28, and the atrioventricular delay timer 40 through the OR circuit 22 such that the atrium stimulation interval timer 28 is made reset and at the same time the atrioventricular delay timer 40 is made to start the time measuring.

In the atrioventricular delay set-value memory 41, a delay time which is allowable for a patient after the atrium is contracted until the ventricle is contracted is set and normally a spontaneous ventricle contraction occurs before the set-value is counted such that the atrioventricular delay timer 40 is made stopped every at that time by the output of the ventricle contraction detector 4. Consequently, the atrioventricular delay timer 40 does not count until the set-value stored in the atrioventricular delay set-value memory 41, so that an output cannot be obtained from the atrioventricular delay comparison portion 42 and an output of the atrioventricular delay comparison portion 42 is not supplied to the ventricle stimulator 3. Therefore, a forced ventricle stimulation is not performed.

If a spontaneous ventricle contraction does not occur within the atrioventricular delay time stored in the atrioventricular delay set-value memory 41, there is no output obtained from the ventricle contraction detector 4, so that the atrioventricular delay timer 40 continues counting without stopping. More specifically, the atrioventricular delay timer 40 continues counting until it reaches the set-value stored in the atrioventricular delay set-value memory 41 and generates an output from the atrioventricular delay comparison portion 42 when it becomes in conformity thereto. The output of the atrioventricular delay comparison portion 42 is transmitted to the ventricle stimulators 3 and the right ventricle 14 is stimulated by the ventricle stimulating electrode 10 through the ventricle lead 9.

On the other hand, when the atrium contraction detector 6 detects the contraction of the right atrium 15, the atrium stimulation interval timer 28 is made reset by the output of the atrium contraction detector 6 through the OR circuit 22. In the atrium stimulation interval set-value memory 29, there is set the time which corresponds to a cardiac cycle duration at the time of normal and if a next atrium contraction is not detected within the time, the measured time of the atrium stimulation interval timer 28 reaches the set-value stored in the atrium stimulation interval set-value memory 29, so that the comparison portion 30 generates an output. The atrium stimulation is performed by the output of the comparison portion 30 and at the same time, the output of the comparison portion 30 is supplied to the nerve stimulation controller 32 through the OR circuit 22 such that the stimulation of the vagus nerve 18 is performed by the nerve stimulator 7. Here, with respect to the strength or repetition-rate of the nerve stimulation, it is adjusted by selecting parameters stored in the nerve stimulation parameter table memory 31 in response to the patient condition. The selection of the parameters is performed by detecting the output of the activity sensor 43 which is represented by an acceleration sensor.

Figure 9:
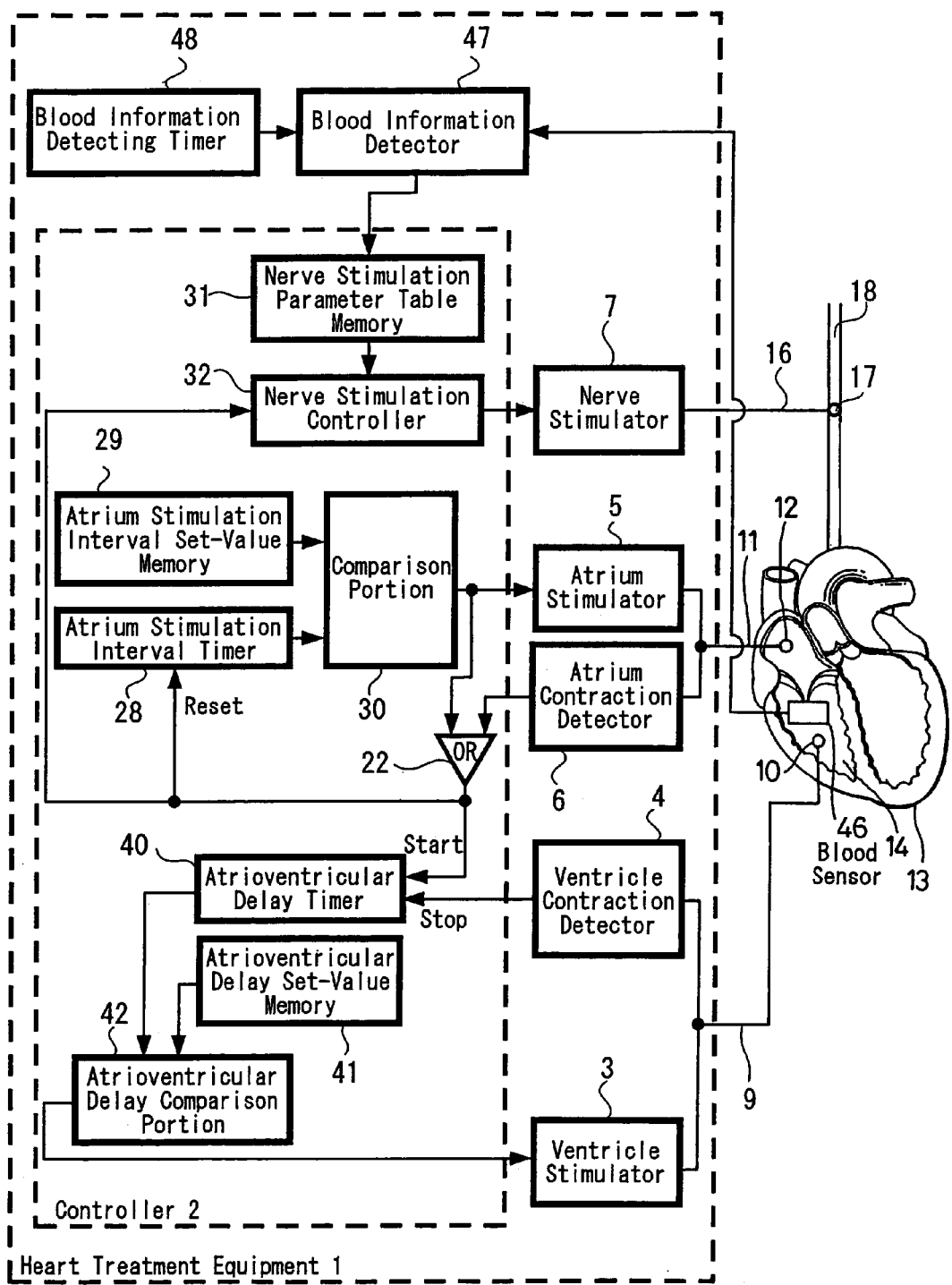
FIG. 9 is a block diagram showing a constitutional example of a fourth exemplified embodiment of a heart treatment equipment according to the present invention.

Next, a fourth exemplified embodiment of the heart treatment equipment according to the present invention will be described using the block diagram of FIG. 9 where the portions same as those in the block diagram of FIG. 8 have the same reference numerals.

The fourth exemplified embodiment is different from the third exemplified embodiment only in the sensor portion which selects the parameters of the nerve stimulation parameter table memory 31. In the fourth exemplified embodiment, a blood sensor 46 which is provided either in the atrium electrode or in the ventricle electrode is used. The living body information detected by the blood sensor 46 includes a central venous temperature, a central venous oxygen saturation, blood pH, a catecholamine level and the like where either of them relates to the level of the autonomic tone (especially sympathetic tone) caused by the physical exercise and mental stress.

The operation of the fourth exemplified embodiment of the heart treatment equipment according to the present invention will be explained hereinafter but the overview explanation of the whole block diagram will be omitted because it is same as that of the third exemplified embodiment shown in FIG. 8. In the fourth exemplified embodiment, a blood sensor 46 which is mounted at the ventricle stimulating/detecting electrode 10 or the ventricle lead 9 provided in the right ventricle 14 is used. In FIG. 9, it is drawn as a separate body with the ventricle stimulating/detecting electrode 10 or the ventricle lead 9 in order to illustrate intelligibly, but it is to be formed as a one body construction therewith in the heart 1.

Aforementioned various blood information relating to the level of the sympathetic tone is detected by the blood sensor 46 arranged in the right ventricle 14 and the detected information is transmitted to the nerve stimulation parameter table memory 31 and parameter selection for controlling the stimulation of the vagus nerve 18 is performed.

Figure 10:
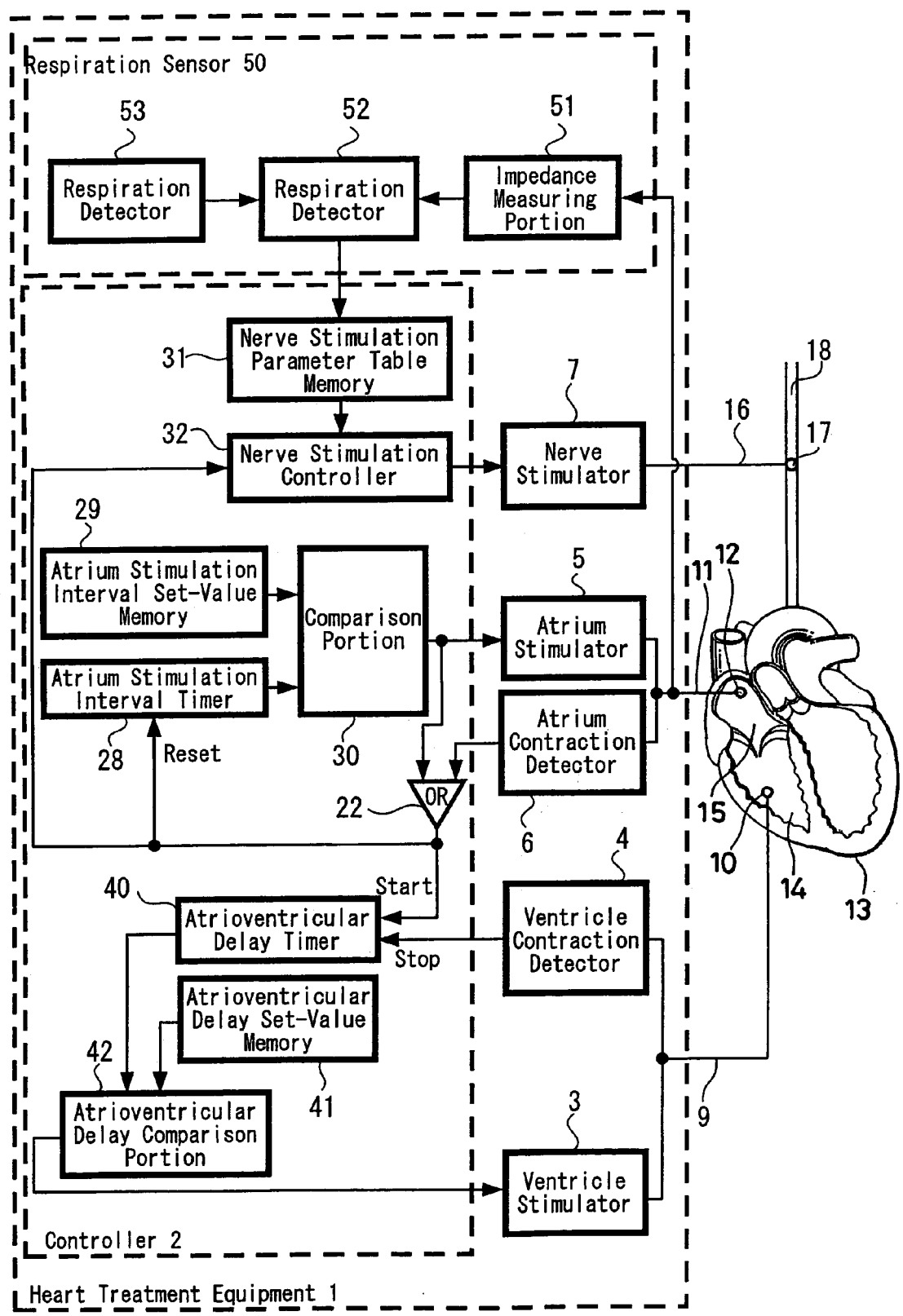
FIG. 10 is a block diagram showing a constitutional example of a fifth exemplified embodiment of a heart treatment equipment according to the present invention.

Next, a fifth exemplified embodiment according to the present invention will be explained with reference to the block diagram shown in FIG. 10. In the exemplified embodiment of FIG. 10, same reference numerals are put to the same blocks as those shown in FIG. 8 and FIG. 9. The fifth exemplified embodiment differs from the difference from the third and the fourth exemplified embodiments in that a respiration sensor 50 which detects living body information for selecting parameters of the nerve stimulation parameter table memory 31 is provided. The respiration sensor 50 is constituted by an impedance measuring portion 51 connected to the atrium lead 11, a respiration detector 52 supplied with an output of the impedance measuring portion 51, and a respiration detecting timer 53 for measuring a timing of the respiration detection. The impedance measuring portion 51 supplies a constant current waveform which has a strength not to stimulate the heart between a titanium-made housing of the heart treatment equipment 1 implanted beneath the skin of the chest and the atrium stimulating/detecting electrode 12 through the atrium lead 11 and measures an impedance by measuring a voltage there between. In this way, the respiration sensor 50 can detect an expansion or a contraction of the chest based on the impedance change between the right atrium 15 and the region, so that it becomes possible to know the patient's respiration. With respect to the respiration sensor 50, it should be noted that it is also possible to know the patient's respiration by connecting the impedance measuring portion 51 and the ventricle lead 9 so as to detect the impedance change between the right ventricle 14 and the chest region.

The operation of aforesaid fifth exemplified embodiment of the heart treatment equipment according to the present invention will be explained hereinafter. When the level of the sympathetic tone is high by a physical exercise or a mental stress, respiration (the number of respiratatory and respiratatory volume) becomes intensive and this is caught as an impedance change by the impedance measuring portion 51 of the respiration sensor 50. The respiration detector 52 handles the impedance waveform measured by the impedance measuring portion 51 every at an appropriate time measured by the respiration detecting timer 53 and the respiratory rate is detected by the speed of the impedance change and the respiratory volume is detected by the amount thereof such that parameters of the nerve stimulation parameter table memory 31 are selected in response to the respiratory rate and the respiratory volume. Then, a signal is emitted from the nerve stimulation controller 32 to the nerve stimulator 7 according to the selected parameters and an appropriate stimulation of the vagus nerve 18 is performed by the nerve stimulator 7.

Figure 11:
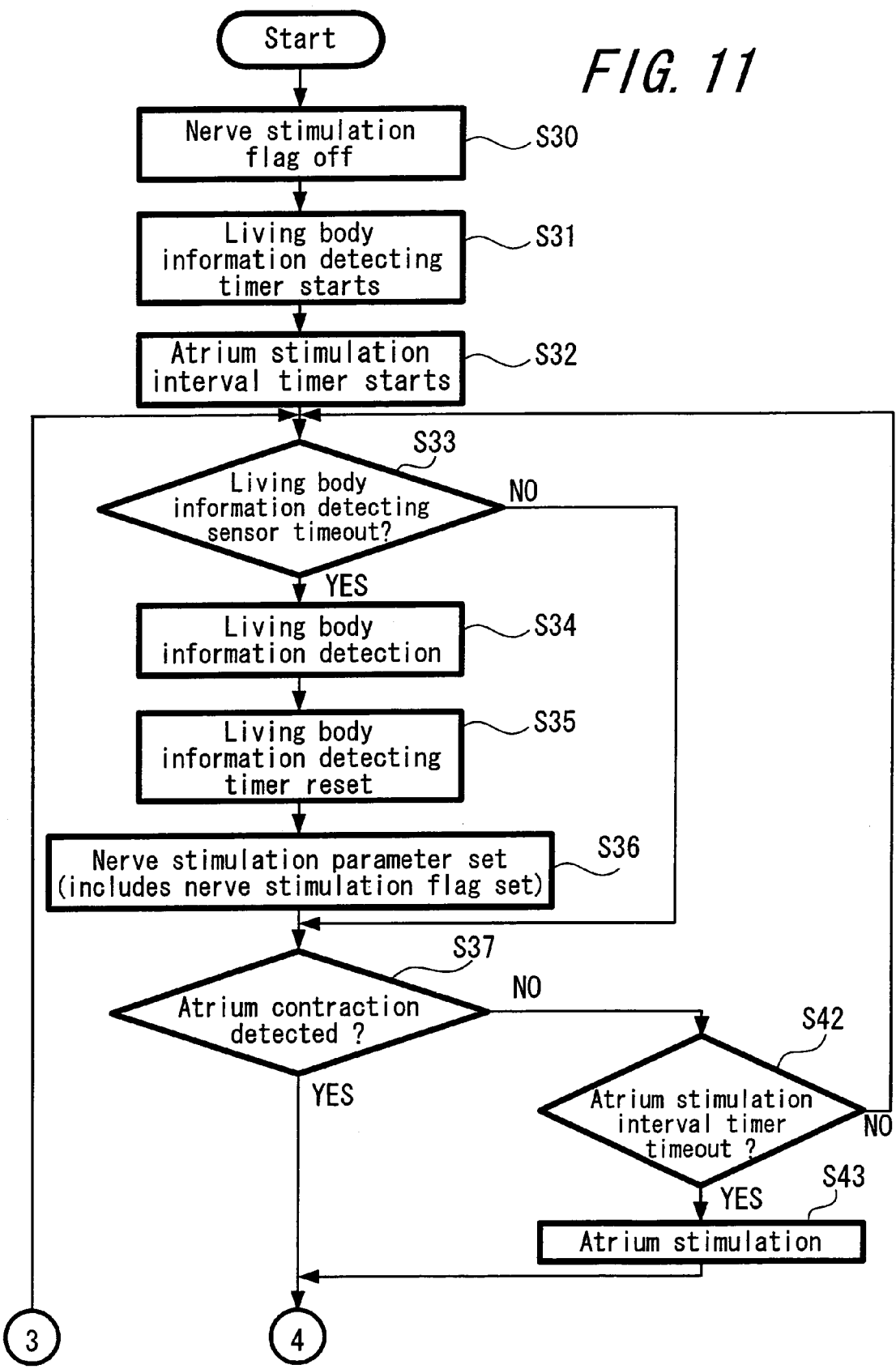
FIG. 11 is a flowchart showing an operation of the third to fifth exemplified embodiments of a heart treatment equipment according to the present invention shown in FIG. 8 to FIG. 10.
Figure 11:
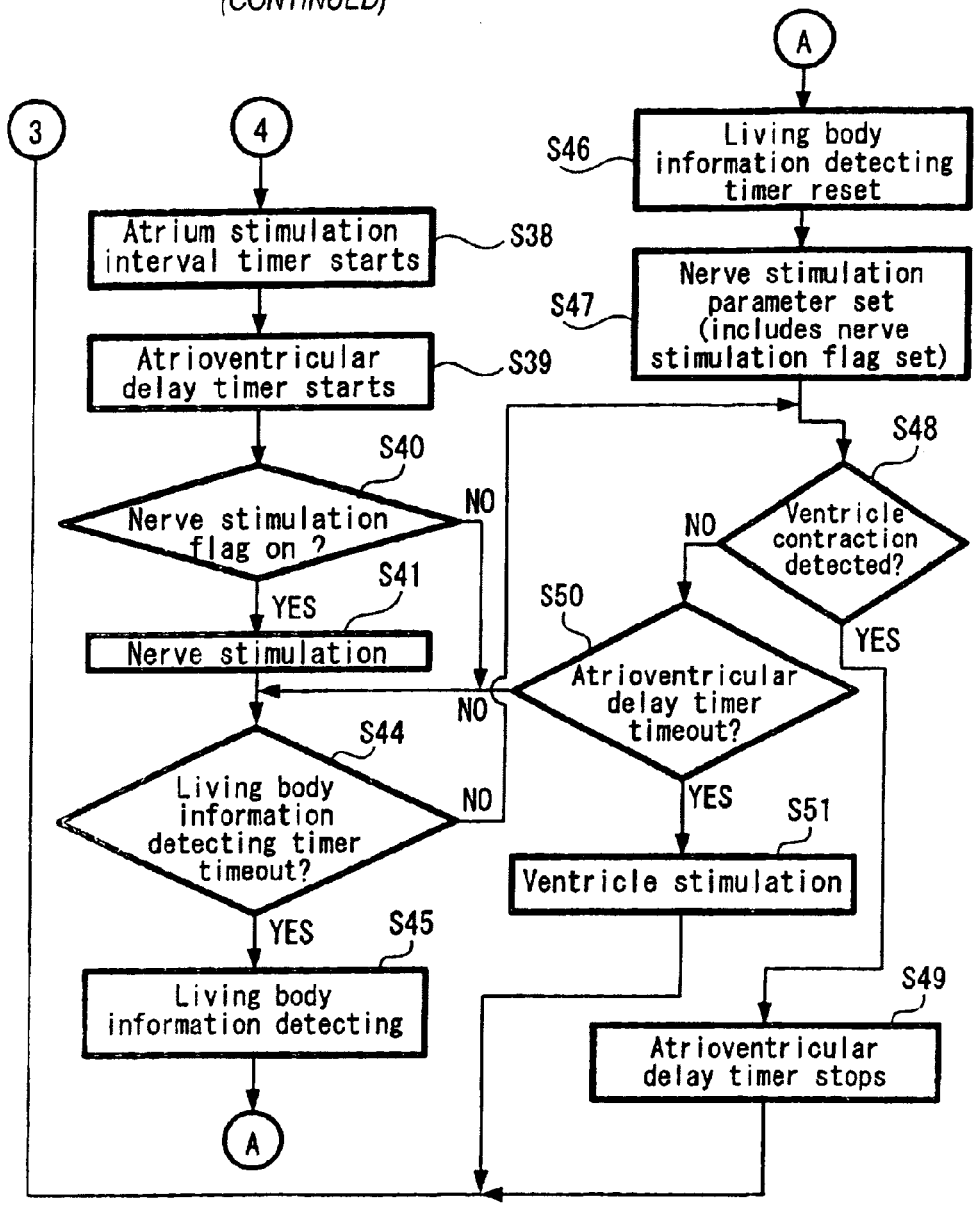

The operations of the third to the fifth exemplified embodiments of the heart treatment equipment according to the present invention shown in FIG. 8 to FIG. 10 will be explained with reference to a flowchart shown in FIG. 11. The different portions among these three exemplified embodiments are sensor portions, so that all of these will be explained as living body information detecting sensors hereinafter. The living body information detecting sensors express an activity sensor, a blood sensor and a respiration sensor respectively corresponding to each exemplified embodiments.

First, the nerve stimulation flag of the nerve stimulation controller 32 is made off (step S30), at the same time a living body information detecting timer is made to start (step S31), and additionally the atrium stimulation interval timer 28 is made reset so as to start the time measuring (step S32).

Next, it is judged whether or not the living body information detecting timer times out (step S33). When the living body information detecting timer times out, living body information is detected by the living body information detecting sensor at the time for detecting the living body information (step S34) and the living body information detecting timer is made reset again (step S35). Then, a nerve stimulation parameter which is optimal for the patient is subsequently selected from the table of the nerve stimulation parameter table memory 31 in accordance with the detection of the living body information in the living body information detecting sensor (step S36). The selection of the nerve stimulation parameter at this time includes a selection of whether or not the nerve stimulation is performed and if the nerve stimulation is performed, the nerve stimulation flag is made on. When it is judged in the judgment step S33 that the living body information detecting timer does not time out, the detection of the living body information is not conducted and the detection of the atrium contraction will be awaited for.

Subsequently, it is judged whether or not the atrium contraction is detected in the atrium contraction detector 6 (step S37). If the atrium contraction is detected, the atrium stimulation interval timer 28 is made reset (step S38), and subsequently the atrioventricular delay timer 40 is made reset so as to start the time measuring (step S39). Next, it is judged whether or not the nerve stimulation flag of the nerve stimulation controller 32 is on (step S40) and if the nerve stimulation flag is on, a signal is emanated from the nerve stimulation controller 32 to the nerve stimulator 7 such that the vagus nerve 18 is stimulated. If the nerve stimulation flag is off in the judgment step S40, the nerve stimulation is not performed and the flow proceeds to a next step.

If it is judged that the atrium contraction is not detected in the judgment step S37, it is judged whether or not the atrium stimulation interval timer 28 time out, that is, whether or not the measured time of the atrium stimulation interval timer 28 exceeds the set-value stored in the atrium stimulation interval set-value memory 29 (step S42). Then, if it is judged that the atrium stimulation interval timer 28 times out, an output is emanated from the comparison portion 30 to the atrium stimulator 5 and the atrium stimulation is performed (step S43).

After the stimulation of the vagus nerve 18 is performed in step S41 it is judged again whether or not the living body information detecting timer times out (step S44). Then, if it is judged that the living body information detecting timer times out, a living body information detection (step S45), a living body information detecting timer reset (step S46) and a nerve stimulation parameter setting (step S47) are subsequently performed similarly as the step S34 to step S36, and next the flow enters a ventricle contraction detecting step (step S48). It should be noted that the selection of the nerve stimulation parameter includes the selection of whether or not the nerve stimulation is performed and if the nerve stimulation is performed, the nerve stimulation flag is made on.

If it is judged that the living body information detecting timer does not time out in the judgment step S44, that is, is judged that the timing for measuring does not come yet, the flow similarly enters the subsequent ventricle contraction detection step (step S48).

Next, if the ventricle contraction is detected in the judgment step S48, the time measuring of the atrioventricular delay timer 40 stops (step S49), and the flow returns to the judgment step S33 again. If the ventricle contraction is not detected in the judgment step S48, it is judged whether or not the atrioventricular delay timer 40 times out, that is, whether or not the set-value stored in the atrioventricular delay set-value memory 41 is exceeded (step S50). If it is judged that the atrioventicular delay timer 40 times out in the judgment step S50, an output is emanated from the atrioventricular delay comparison portion 42 to the ventricle stimulator 3 and the ventricle stimulation is performed (step S51) After this ventricle stimulation is performed, the flow returns to the judgment step S33 again and if it is judged in the judgment step S50 that the atrioventricular delay timer 40 does not time out, the flow returns to the judgment step S44 and it is judged again whether or not the living body information detecting timer times out.

Figure 12:
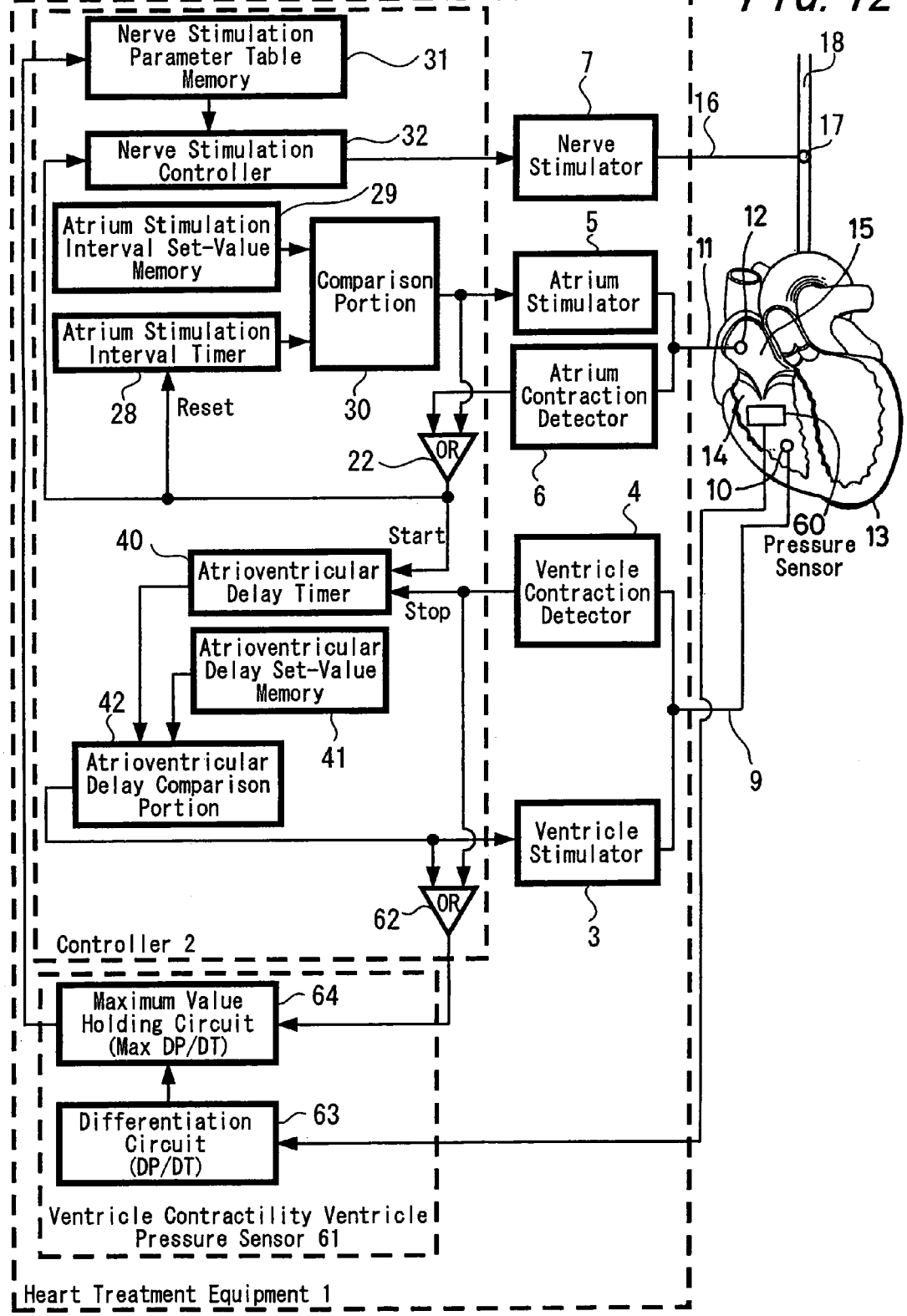
FIG. 12 is a block diagram showing a constitutional example of a sixth exemplified embodiment of a heart treatment equipment according to the present invention.

FIG. 12 is a block diagram showing a sixth exemplified embodiment of a heart treatment equipment according to the present invention. It differs from the third to the fifth exemplified embodiment shown in FIG. 8 to FIG. 10 in a portion where the rate of change of the ventricle pressure (the first derivative of the ventricle pressure) dp/dt of the pressure inside the ventricle is detected for the kind of the living body information. The same reference numerals are used for the same constitutional portions.

In FIG. 12 which shows the sixth exemplified embodiment of the present invention, it is newly added with a pressure sensor 60 provided in the right ventricle 14, a ventricle contractility pressure sensor 61 for receiving an output of the pressure sensor 60, and an OR circuit 62 which is supplied with an output of the ventricle contraction detector 4 and an output of the atrioventricular delay comparison 42, that is, with information instructing the ventricle stimulation and which supplies an output thereof to the ventricle contractility pressure sensor 61. Then, the ventricle contractility pressure sensor 61 is constituted by a differentiation circuit 63 for differentiating the signal from the pressure sensor 60 and a maximum value holding circuit 64 for monitoring the output of the differentiation circuit 63 at the output timing of the OR circuit 62 and for holding its maximum value.

The operation of the sixth exemplified embodiment according to the present invention will be explained hereinafter. The pressure sensor 60 measures pressure when the ventricle is contracted and is normally provided in the ventricle stimulating/detecting electrode 10 or the ventricle lead 9. Then, the intraventicular pressure is measured by the pressure sensor 60 where the differentiated signal of the signal from the pressure sensor 60 is dp/dt and the maximum value of the differentiated signal held in the maximum value holding circuit 64 is max dp/dt. With reference to this differentiation maximum value max dp/dt, a maximum value during a period after the output timing of the OR circuit 62, that is, after the timing of the detection of the ventricle contraction or the stimulation to the ventricle until a predetermined period, for example, 100 ms is to be held. Then, the held max dp/dt is transmitted to the nerve stimulation parameter table memory 31 of the controller 2 and optimal stimulation parameters for the patient are selected in accordance with that value.

Here, the max dp/dt of the ventricle increases in accordance with the intense physical exercise and the mental stress, so that it becomes possible to sense how much is the physical exercise and/or the mental stress. By utilizing this characteristic, a strong nerve stimulation is performed when the max dp/dt is large and only a weak nerve stimulation is performed or a nerve stimulation is stopped when the max dp/dt is small.

Figure 13:
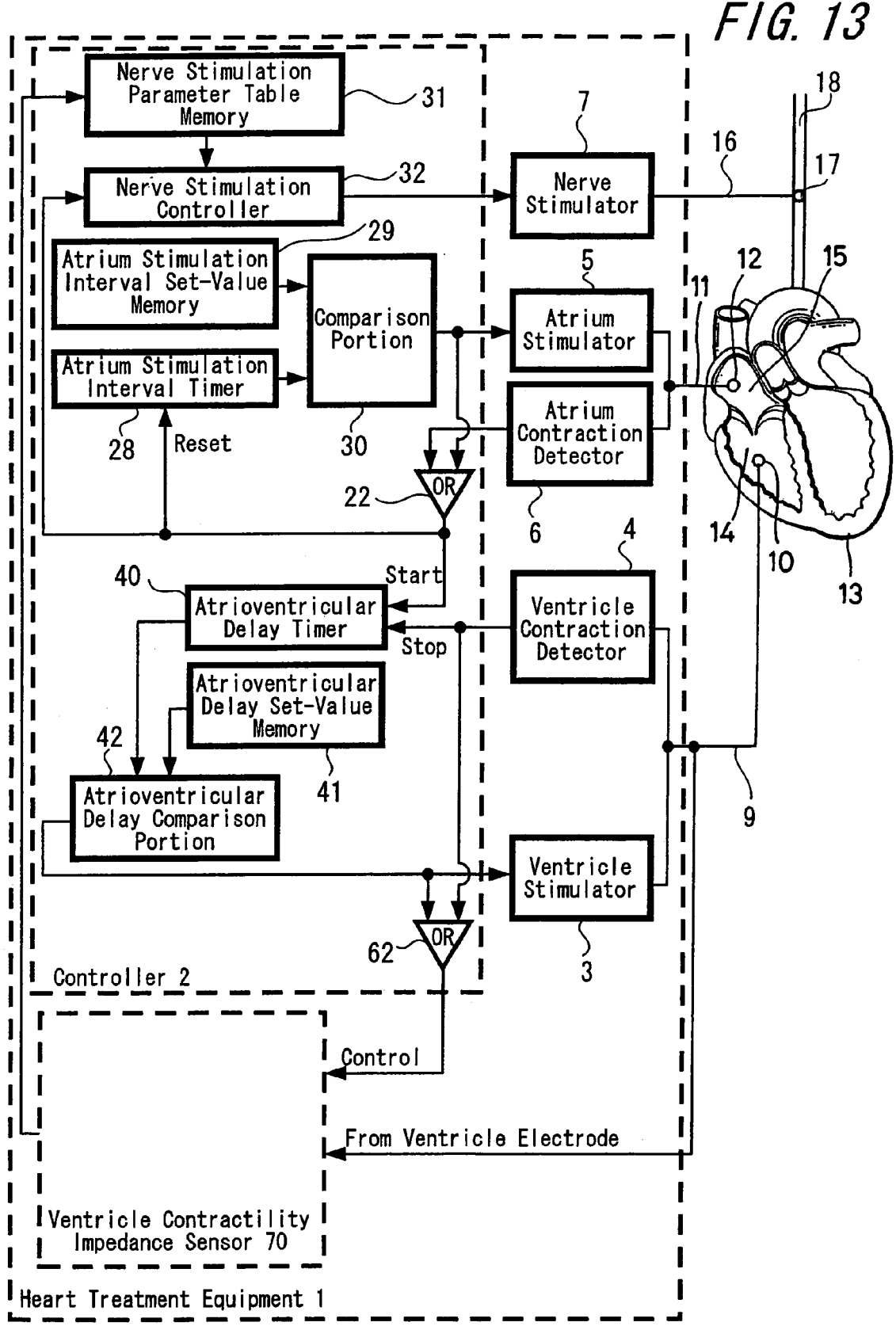
FIG. 13 is a block diagram showing a constitutional example common to a seventh and an eighth exemplified embodiments of a heart treatment equipment according to the present invention.

FIG. 13 is a block diagram showing a seventh exemplified embodiment of the heart treatment equipment according to the present invention. The difference from the sixth exemplified embodiment shown in FIG. 12 lies in the kind of the living body information and its detecting sensor portion. In the sixth exemplified embodiment, the maximum rate of change of the intraventicular pressure max dp/dt was used for the living body information, but a ventricle contractility impedance sensor 70 is used in the seventh *exemplified embodiment shown in FIG. 13. As other block constitutions are all the same as those of the sixth exemplified embodiment, the same reference numerals are used for designating the same block constitutions.

The embodied examples of the ventricle contractility impedance sensor 70 are shown in FIG. 14 and FIG. 15. FIG.

14 shows an example of a ventricle pre-ejection period sensor 71 and FIG. 15 shows an example of a stroke volume sensor 75.

The embodiment where the ventricle pre-ejection period sensor 71 of FIG. 14 is used as the ventricle contractility impedance sensor 70 of FIG. 13 is designated as a seventh exemplified embodiment according to the present invention and this will be explained hereinafter.

The ventricle pre-ejection period is the time after the electric ventricle contraction (ventricle contraction detection or ventricle stimulation) stars until the ventricle actually starts the blood ejection. Based on this ventricle pre-ejection period it is possible to sense how much the physical exercise or the mental stress is.

The ventricle pre-ejection period sensor 71 is constituted by pre-ejection period measuring portion 72 for starting the time measuring triggered by the ventricle contraction detection or the ventricle stimulation, an impedance measuring portion 73 for monitoring the volume change of the ventricle, and a ventricle ejection detector 74 receiving an output of the impedance measuring portion 73 for judging that the blood ejection has started when there is a predetermined decrease in the ventricle volume.

The operation of the seventh exemplified embodiment will be explained hereinafter, and in FIG. 13, an output of the ventricle contraction detector 4 and an output of the atrioventricular delay comparison portion 42 are supplied to the OR circuit 62. Consequently, an output is obtained at the OR circuit 62 when the ventricle contraction is detected or the ventricle stimulation is performed and this output is supplied to the pre-ejection period measuring portion 72 of the ventricle pre-ejection period sensor 71 (FIG. 14) where the measurement of the pre-ejection period is started. Then, the ventricle stimulating/detecting electrode 10 is connected to the impedance measuring portion 73 of FIG. 14 by means of the ventricle lead 9 and the impedance measuring portion 73 detects the ventricle volume change as an impedance change when the ventricle volume changes.

The output of the impedance measuring portion 73 is transmitted to the ventricle ejection detector 74 and the ventricle ejection detector 74 monitors the output form the impedance measuring portion 73, that is, the impedance change such that it judges that a blood ejection started when there is a predetermined decrease in the ventricle volume and it stops the time measuring of the pre-ejection period measuring portion 72. This measured ventricle pre-ejection period is transmitted to the nerve stimulation parameter table memory 31 of FIG. 13 and parameters for an optimal nerve stimulation for the patient are selected in response to the ventricle pre-ejection period. This pre-ejection period is made shorter in accordance with the physical exercise or the mental stress, so that the vagus nerve stimulation is made strong when the ventricle pre-ejection period is short.

FIG. 15 is a block diagram showing a constitution of a stroke volume sensor 75 which shows one example of the ventricle contractility impedance sensor 70 shown in FIG. 13.

The stroke volume is a quantity subtracting the end-systolic volume from the end-diastolic volume for one cardiac cycle and it becomes also possible from this stroke volume to know how much is the physical exercise or the mental stress is.

The embodiment where the stroke volume sensor 75 of FIG. 15 is adopted as the ventricle contractility impedance sensor 70 of FIG. 13 is designated as an eighth exemplified embodiment according to the present invention and this will be explained hereinafter.

The stroke volume sensor 75 shown in FIG. 15 is constituted by an end-diastolic volume detector 76 for detecting the ventricle end-diastolic volume triggered by the ventricle contraction detection or the ventricle stimulation, an impedance measuring portion 77 for monitoring the ventricle volume change based on the impedance change, an end-systolic volume detector 78 for detecting the minimum value of the ventricle volume as a end-systolic volume from the output of the impedance measuring portion 77 subsequent to the end-diastolic volume detection, and a stroke volume measuring portion 79 for measuring the stroke volume by subtracting the output of the end-systolic volume detector 78 from the output of the end-diastolic volume detector 76.

The operation of the eighth exemplified embodiment according to the present invention will be explained hereinafter, and in FIG. 13, an output is obtained at the OR circuit 62 when the ventricle contraction is detected or the ventricle stimulation is performed where this output is supplied to the end-diastolic volume detector 76 of the stroke volume sensor 75 (FIG. 15). On the other hand, the impedance measuring portion 77 connected to the ventricle stimulating/detecting electrode 10 determines the ventricle volume from the measured impedance and this is transmitted to the end-diastolic volume detector 76 and the end-systolic volume detector 78. The end-diastolic volume detector 76 detects the ventricle volume at the time of the ventricle contraction detection or at the time of the ventricle stimulation according to the output of the impedance measuring portion 77 and makes that volume as a ventricle end-diastolic volume. Further, the end-systolic volume detector 78 monitors the output of the impedance measuring portion 77 and detects the minimum value of the ventricle volume as a ventricle end-systolic volume.

Then, in the stroke volume measuring portion 79, an output difference between the end-diastolic volume detector 76 and the end-systolic volume detector 78, that is, the difference between the ventricle end-diastolic volume and the ventricle end-systolic volume is measured and this operated result is transmitted to the nerve stimulation parameter table memory 31 of FIG. 13 as a stroke volume. Then, parameters are selected for the optimum nerve stimulation for the patient in response to the measured stroke volume. This stroke volume becomes more or less in response to the physical exercise or the mental stress, so that the vagus nerve stimulation is made strong when the stroke volume is large.

Figure 16:
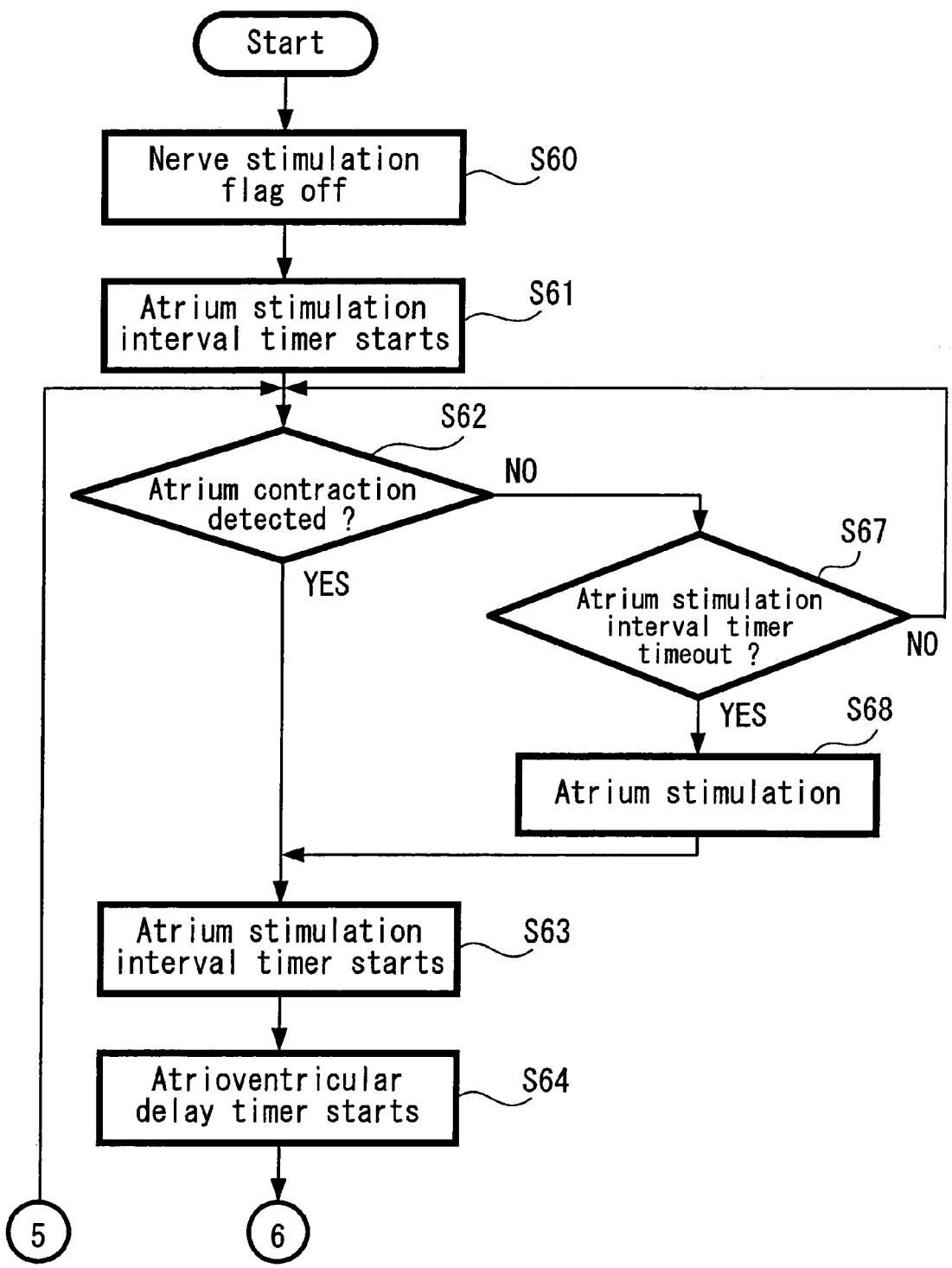
FIG. 16 is a flowchart for explaining an operation of the sixth to eighth exemplified embodiments of a heart treatment equipment according to the present invention shown, in FIG. 12 to FIG. 15.
Figure 17A:
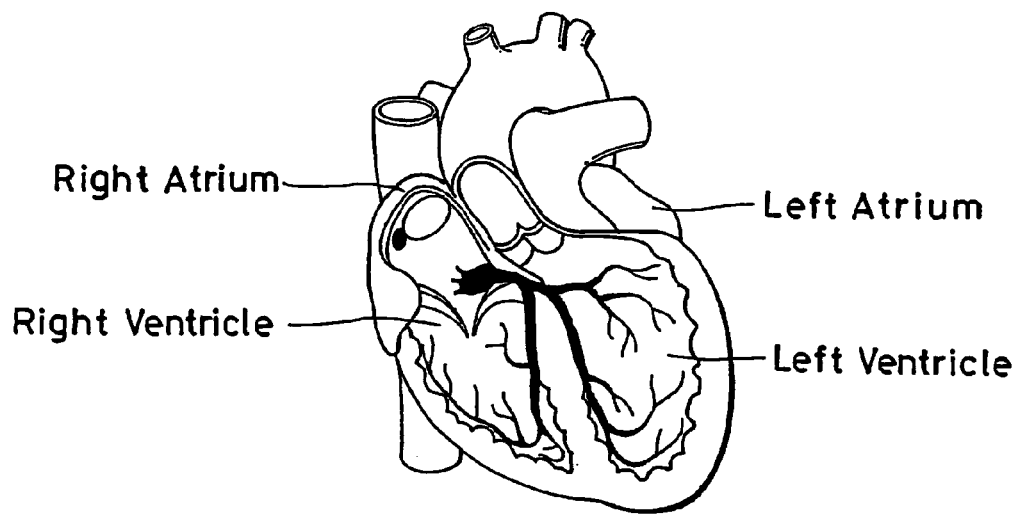
FIG. 17A is a diagram showing a heart construction and FIG. 17B is an example of an electrocardiogram measured from electrodes placed on the skin in specific locations.
Figure 17B:
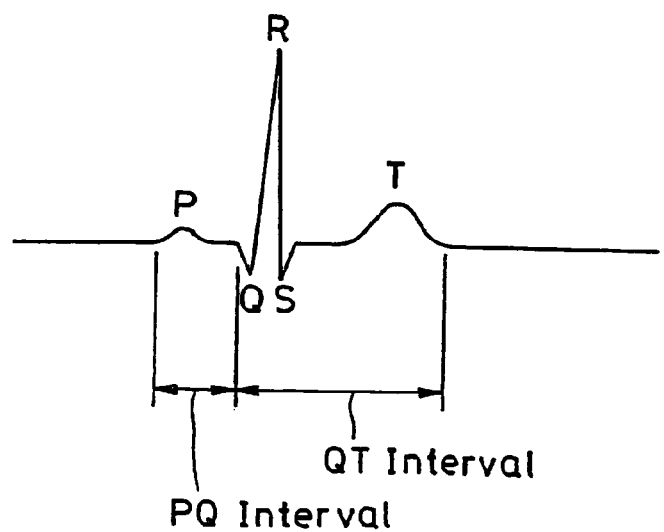

Next, the operations of the sixth to the eighth exemplified embodiments according to the present invention shown in FIG. 12 to FIG. 15 will be explained in detail using the flowchart of FIG. 16.

First, the nerve stimulation flag of the nerve stimulation controller 32 is made off (step S60) and additionally, the atrium stimulation interval timer 28 is made reset so as to start the time measuring (step S61).

In this condition the initial setting is completed and next it is judged in the atrium contraction detector 6 whether or not the atrium contraction is detected (step S62). If the atrium contraction is detected, the atrium stimulation interval timer 28 is made reset (step S63) and the atrioventricular delay timer 40 is subsequently made reset so as to start the time measuring (step S64). Next, it is judged whether the nerve stimulation flag of the nerve stimulation controller 32 is on (step S65) and if the nerve stimulation flag is on, a signal is emanated from the nerve stimulation controller 32 to the nerve stimulator 7 and the stimulation of the vagus nerve 18 is performed (step S66). If the nerve stimulation flag is off in the judgment step S65, the nerve stimulation is not performed and the flow proceeds to the next step.

If it is judged in the judgment step S62 that the atrium contraction is not detected, it is judged whether or not the atrium stimulation interval timer 28 times out, that is, whether or not the measured time of the atrium stimulation interval timer 28 exceeds the set-value stored in the atrium stimulation interval set-value memory 29 (step S67). Then, if it is judged that the atrium stimulation interval timer 28 times out, an output is emanated from the comparison portion 30 to the atrium stimulator 5 and the atrium stimulation is performed (step S68).

Subsequently, it is judged whether or not the ventricle contraction is performed (step S69). Then, if the ventricle contraction is detected, the time measuring of the atrioventricular delay timer 40 is made stopped (step S70). If the ventricle contraction is not detected in the judgment step S69, it is judged whether or not the atrioventricular delay timer 40 times out, that is, whether or not the set-value stored in the atrioventricular delay set-value memory 41 is exceeded (step S71). If it is judged in the judgment step S71 that the atrioventicular delay timer 40 times out, an output is emanated from the atrioventricular-delay comparison portion 42 to the ventricle stimulator 3 and the ventricle stimulation is performed (step S72). When this ventricle stimulation is performed and after the time measuring of the atrioventricular delay timer 40 is made stopped in the step S70, the detection of the ventricle pressure (sixth exemplified embodiment), of the pre-ejection period (seventh exemplified embodiment) and of the stroke volume (eighth exemplified embodiment) is conducted in each sensor of the exemplified embodiments (step S73). Then, the living body information amount relating to the physical exercise, the mental stress and the like detected by the sensor of each exemplified embodiments are transmitted to the nerve stimulation parameter table memory 31 such that optimal nerve stimulation parameters for the patient are selected (step S74). Here, the selection of the nerve stimulation parameters includes the selection whether or not the nerve stimulation is performed and when the nerve stimulation is performed, the nerve stimulation flag is made on.

In the above description, a plurality of exemplified embodiments where the vagus nerve is controlled by detecting living body information are explained with reference to block diagrams and flowcharts, but the present invention is not limited by those exemplified embodiments and it is possible to control the nerve stimulation parameters by detecting various living body information which shows the level of the sympathetic tone.

Next, a ninth exemplified embodiment of the heart treatment equipment according to the present invention will be explained in detail with reference to FIG. 19 and FIG. 20. It should be noted also in this exemplified embodiment that same reference numerals are put for the same constitutional portions as those of the first to the eighth exemplified embodiments.

Figure 19:
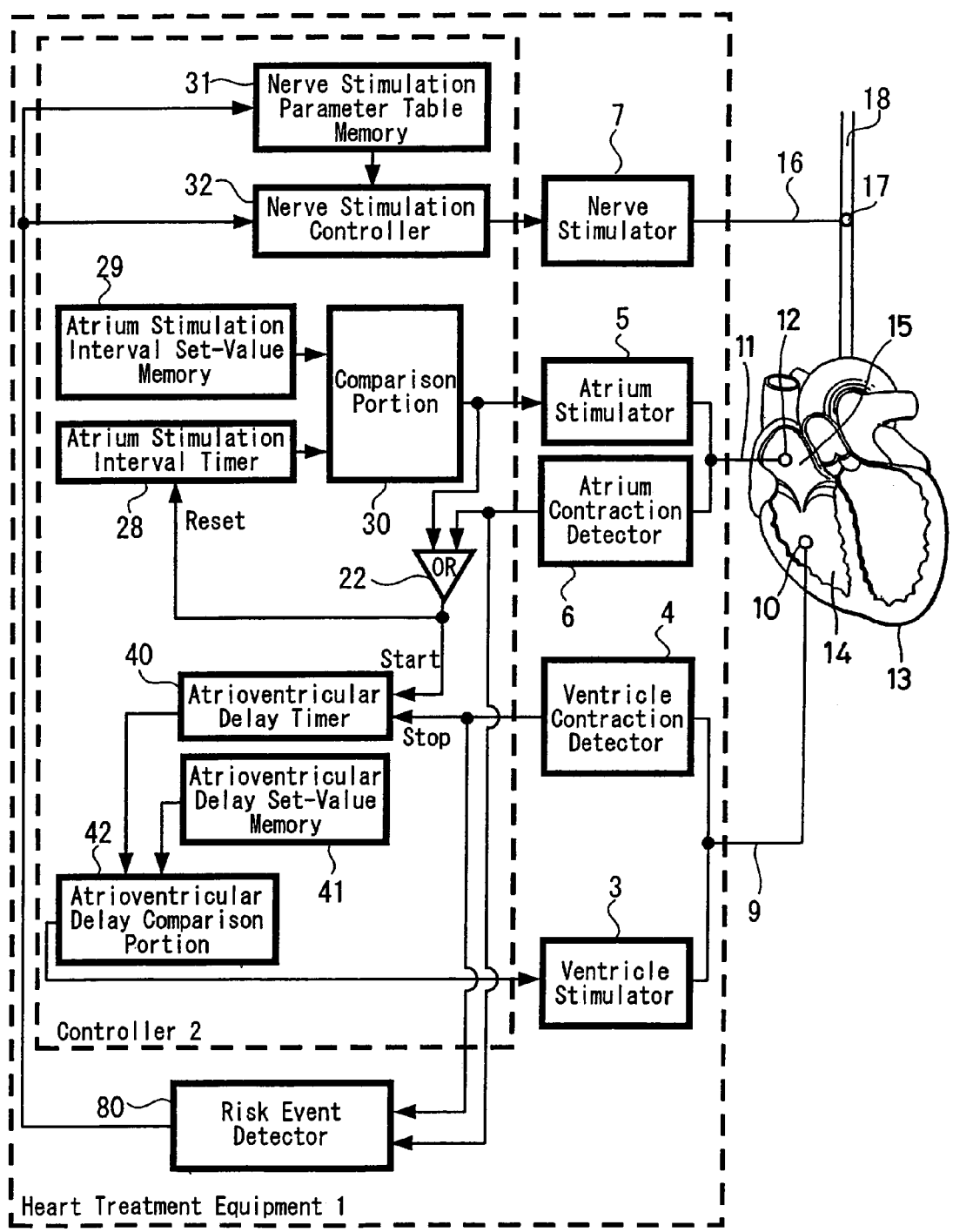
FIG. 19 is a block diagram showing a constitutional example of a ninth exemplified embodiment of a heart treatment equipment according to the present invention.
Figure 20:
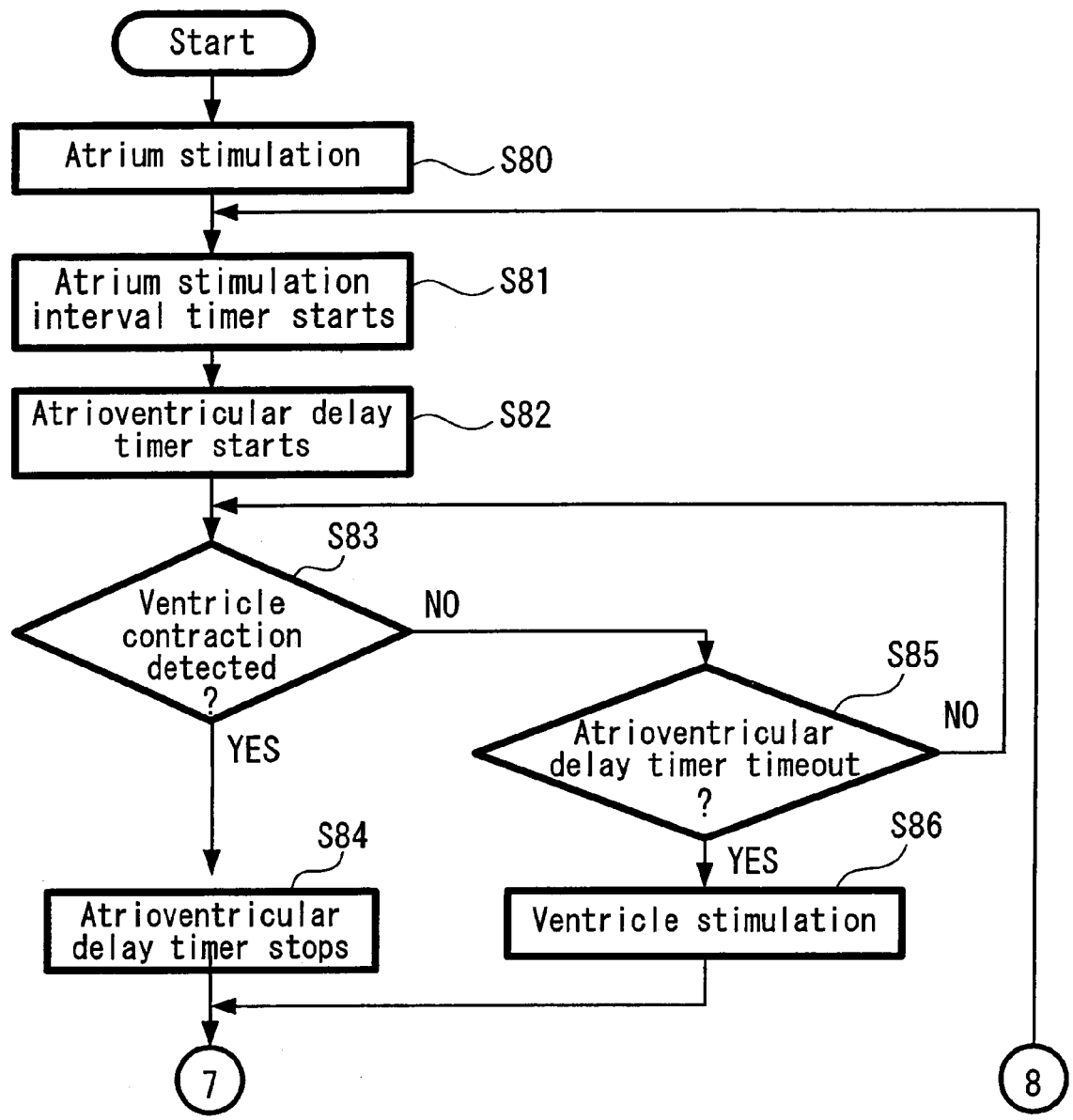
FIG. 20 is a flowchart showing a constitutional example of the ninth exemplified embodiment of a heart treatment equipment according to the present invention shown in FIG. 19.
Figure 20:
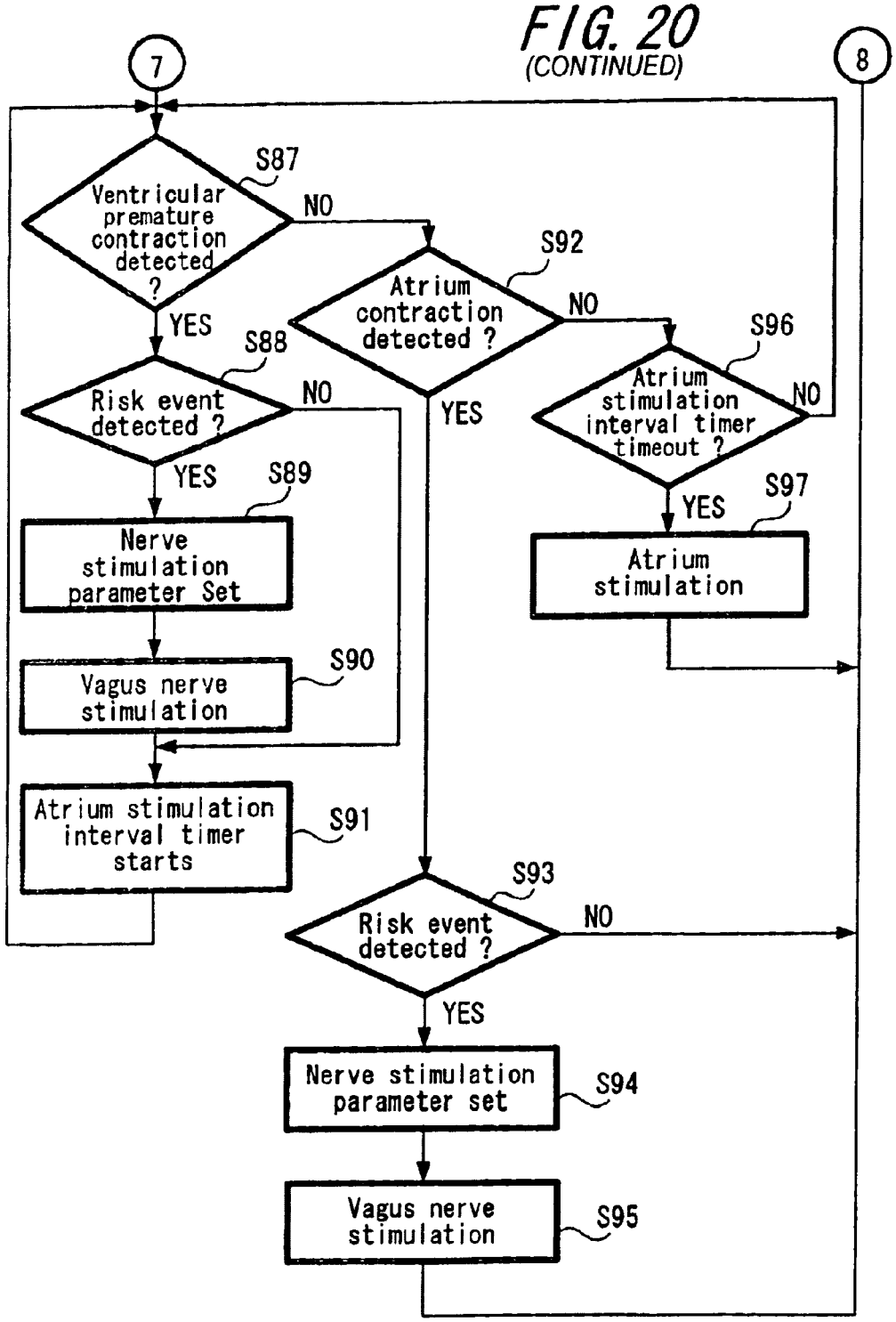

FIG. 19 is a constitutional block diagram showing the ninth exemplified embodiment of the heart treatment equipment according to the present invention. In this ninth exemplified embodiment, the difference from the first to the eighth exemplified embodiments lies in that there is provided with a risk event detector 80 which controls the nerve stimulation parameter table memory 31 and the nerve stimulation controller 32 in response to the outputs of the ventricular contraction detector 4 and the atrium contraction detector 6.

The operation of the ninth exemplified embodiment will be explained hereinafter, and in FIG. 19, the risk event detector 80 judges whether or not the VT/VF (ventricle tachycardia/ventricle fibrillation) risk event exists in accordance with the information related to the ventricle event detected by the ventricle contraction detector 4 and the information related to the atrium event detected by the atrium contraction detector 6. As a representative VT/VF risk event, there are events such as a heart rate increase and a heart rate change which go over a predetermined rate and a atrium premature contraction and a ventricular premature contraction where a heartbeat occurs prior to the time when the next normal heartbeat would be expected to appear. Then, the detected risk event signal is transmitted to the nerve stimulation parameter table memory 31 and the nerve stimulation controller 32 of the controller 2, and in the nerve stimulation parameter table memory 31, nerve stimulation parameters are selected according to the kinds of the detected risk event and these selected parameters are transmitted to the nerve stimulation controller 32; in the nerve stimulation controller 32, a signal is transmitted to the nerve stimulator 7 at the detection timing of the VT/VF risk event in accordance with the various nerve stimulation parameters selected by the nerve stimulation parameter table memory 31; and the stimulation of the vagus nerve 18 is performed by means of the nerve electrode 16 and the nerve stimulation electrode 17.

Table 4 shows a control example of the nerve stimulation parameters according to the VT/VF risk event. When the VT/VF risk event is detected, the nerve stimulation flag is made set and the nerve stimulation parameters are controlled in response to the kinds of the detected VT/VF risk events so as to perform the stimulation of the vagus nerve 18. Table 4 is an example of controlling the number of pulses for performing a nerve stimulation in accordance with the risk level of the VT/VF risk event. As VT/VF risk events, atrium heart rate increase more than (80 times/min), one atrium premature contraction, one ventricular premature contraction, 2 consecutive ventricular premature contractions and 3 or more consecutive ventricular premature contractions are set or selected where the number of nerve stimulations is increased by making the number of pulses many in order to strongly increase the vagus tone in case of the 3 or more ventricular premature contractions of an event which is high risk for inducing the ventricle tachycardia or the ventricle fibrillation. On the other hand, it is set so as to make the number of the stimulations small in case of the heart rate increase or one premature contraction of an event which is relatively a low risk. In this case, it is needless to say that the nerve stimulation parameters for controlling can be selected from other parameters than the number of pulses according to this example as a single parameter or as a combination of a plurality of parameters.

TABLE 4

| | Nerve Stimulation Parameters | | | | | | | |
|---|---|---|---|---|---|---|---|---|
| VT/VF risk event | Number of Pulses | Delay Time | Amp. | Pulse Width | Period between Pulses | Repetitive Number of Times | Pause Time | Nerve Stimul. Flag |
| Atrium heart rate more than 80 times/min | 1 | 0 msec | 3 V | 1 msec | — | — | — | on |
| One atrial premature contraction | 2 | 0 msec | 3 V | 1 msec | 50 msec | 1 | — | on |

TABLE 4-continued

| | Nerve Stimulation Parameters | | | | | | |
|---|---|---|---|---|---|---|---|
| VT/VF risk event | Number of Pulses | Delay Time | Amp. | Pulse Width | Period between Pulses | Repetitive Number of Times | Pause Time | Nerve Stimul. Flag |
| One ventricular premature contraction | 3 | 0 msec | 3 V | 1 msec | 50 msec | 1 | — | on |
| Two consecutive ventricular premature contractions | 4 | 0 msec | 3 V | 1 msec | 50 msec | 1 | — | on |
| 3 or more ventricular premature contractions | 5 | 0 msec | 3 V | 1 msec | 50 msec | 1 | — | on |

For the VT/VF risk event other than the above, it is possible to additionally consider the coupling time (time after the adjacent event until a premature contraction where the shorter or the more variable-this time the more higher the risk is) of the premature contraction or the shape of the premature contraction waveform (the risk is high when the shape becomes different at every occurrence) and the detection of the early after-depolarization or the delay after-depolarization which causes a triggered activity considered to be a generation mechanism of the VT/VF, which are obtained by directly analyzing the intracardiac electrogram in the heart obtained from the atrium detecting electrode 12 or the ventricle detecting electrode 10.

It should be noted that it will be explained here on an assumption that the increase of the atrium heart rate more than the basic rate (rate corresponding to the set-value stored in the atrium stimulation interval set-value memory 29) and the ventricular premature contraction are set as the event for judging whether or not the VT/VF risk event exists.

First, a forced atrium stimulation is performed by the atrium stimulator 5 (step S80), the time measuring of the atrium stimulation interval timer 28 starts (step S81), and the time measuring of the atrioventricular delay timer 40 starts (step S82). Next, it is judged whether or not the ventricle contraction is detected (step S83) and if the ventricle contraction is detected, the time measuring of the atrioventricular delay timer 40 stops (step S84). If the ventricle contraction is not detected in the judgment step S83, it is judged whether or not the atrioventricular delay timer 40 times out, that is, whether or not the set-value stored in the atrioventricular delay set-value memory 41 is exceeded (step S85). If it is judged in the judgment step S85 that the atrioventicular delay timer 40 times out, an output is emanated from the atrioventricular delay comparison portion 42 to the ventricle stimulator 3 and the ventricle stimulation is performed (step S86).

In a next judgment step S87, it is judged whether or not the ventricular premature contraction is detected. More specifically, if a ventricle contraction is detected again subsequently to the ventricle event of the ventricle stimulation or the ventricle contraction, it is judged that a ventricular premature contraction occurs and it is judged by the risk event detector 80 whether or not it is a risk event (step S88). It is judged in the risk event detector 80 whether or not the VT/VF risk event occurred by checking a predetermined condition, for example, the number of times of the premature contraction, continuously occurred number of times of the premature contraction, variability of the coupling time and the like which happened in a predetermined period. Then, if it is judged that a VT/VF risk event occurred, the kind of the VT/VF risk event is determined and a signal is transmitted to the nerve stimulation parameter table memory 31 and the nerve stimulation controller 32, so that in the nerve stimulation parameter table memory 31, the nerve stimulation parameter according to the, judged kind of the VT/VF risk event is set in the nerve stimulation controller 32 (step S89) and in the nerve stimulation controller 32, the nerve stimulator 7 is instructed to stimulate the vagus nerve 18 according to the set nerve stimulation parameter at the detection timing of the VT/VF risk event (step S90). Then, the atrium stimulation interval timer 28 is made reset so as to start the time measuring (step S91).

If the ventricular premature contraction is not detected in the judgment step S87, the detection of the atrium contraction by the atrium contraction detector 6 is awaited (step S92) and if the atrium contraction is detected earlier than the time when the atrium stimulation interval timer 28 reaches the basic rate interval (set-value stored in the atrium stimulation interval set-value memory 29), it is judged by the risk event detector 80 whether or not the VT/VF risk event exists (step S93). In this case, the risk event detector 80 judges by a predetermined condition such as a condition of, for example, a persistent atrium heart rate increase more than a predetermined rate for a predetermined period and an atrium heart rate change more than a predetermined rate change. If it is judged that a VT/VF risk event exists, the kind of the VT/VF risk event is determined and a signal is transmitted to the nerve stimulation parameter table memory 31 and the nerve stimulation controller 32 such that in the nerve stimulation parameter table memory 31, a nerve stimulation parameter according to the judged kind of the VT/VF risk event is set in the nerve stimulation controller 32 (step S94) and in the nerve stimulation controller 32, the nerve stimulator 7 is instructed to stimulate the vagus nerve 18 according to the nerve stimulation parameter at the detection timing of the VT/VF risk event (step S95).

In the judgment step S92, if the atrium stimulation interval timer 28 reaches the basic rate interval (set-value stored in the atrium stimulation interval set-value memory 29) with a situation that the atrium contraction is not detected (step S96), the comparison portion 30 instructs the atrium stimulator 5 to perform the atrium stimulation (step S97).

In the above description, an exemplified embodiment where the stimulation of the vagus nerve is controlled by detecting a VT/VF risk event is explained with reference to a block diagram and a flowchart, but the present invention is not limited by the exemplified embodiment and it is possible to control the nerve stimulation parameters by detecting an event which directly induces a ventricle tachycardia or a ventricle fibrillation or various events which are known as a precursor of a ventricle tachycardia or a ventricle fibrillation.

It should be noted that in the first to the ninth exemplified embodiments according to the present invention, examples directed to applications to the DDD MODE of the dual chamber cardiac pacemakers are raised or picked up, but the present invention is not limited by these embodiments and it is applicable to all operation modes of the cardiac pacemakers. Further, the present invention is not limited to the cardiac pacemakers and it is applicable to a heart treatment equipment such as an implantable cardioverter defibrillator where a vagus nerve stimulation mechanism is provided.

As mentioned above, according to the present invention, the level of the patient sympathetic tone caused by an exercise or mental stress is caught or known by various living body information such that it becomes possible to perform the vagus nerve stimulation appropriately and delicately according to that level of the sympathetic tone, so that enormous effects such as avoidance from the side effects and the heart rate too much lowering caused by the nerve stimulation and the power consumption saving are obtained.

Furthermore, according to the present invention, it becomes possible to perform medical treatment effectively by controlling the stimulation waveform parameters of the vagus nerve stimulation so as to adjust the exerted tone of the parasympathetic nerve in response to the detected VT/VF risk event.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A heart treatment equipment for treating a patient comprising:
   a nerve stimulator for generating a nerve stimulating signal for stimulating a vagus nerve;
   a sensor for sensing an intensity of physical exercise or mental stress of the patient; and
   a controller connected to said nerve stimulator and said sensor,
   wherein said controller controls said nerve stimulator in response to an output of said sensor such that when the intensity of the physical exercise or the mental stress is relatively high, a relatively strong nerve stimulation is performed and when the intensity of the physical exercise or the mental stress is relatively low, a relatively weak nerve stimulation is performed or no nerve stimulation is performed, wherein said controller comprises a nerve stimulation parameter table memory at which is memorized at least one table relating a plurality of nerve stimulation parameters to the intensity sensed by said sensor, said controller controlling said nerve stimulator based on the nerve stimulation parameters selected from the nerve stimulation parameter table memory.

2. A heart treatment equipment according to claim 1, wherein said plurality of nerve stimulation parameters stored in said nerve stimulation parameter table memory are a plurality of stored values with respect to at least one of a period between pulses, a pulse width, a number of pulses, a pulse current, a pulse voltage, a delay time, a rest time and a repetitive number or with respect to a multiple combination chosen from these.

3. A heart treatment equipment according to claim 1, wherein said sensor detects a ventricle contractility.

4. A heart treatment equipment according to claim 3, wherein the ventricle contractility is related to one of a QT interval, an intracardiac electrogram area, a pre-ejection period, a stroke volume and a ventricle pressure.

5. A heart treatment equipment according to claim 3, wherein said controller controls said nerve stimulator so as to stop the generation of said nerve stimulating signal when the ventricle contractility is out of a predetermined range.

6. A heart treatment equipment according to claim 1, wherein said sensor senses an activity.

7. A heart treatment equipment according to claim 1, wherein said sensor senses a respiration.

8. A heart treatment equipment according to claim 1, wherein said sensor senses a blood parameter.

9. A heart treatment equipment according to claim 1, further comprising a heart stimulator for generating a heart stimulating pulse for stimulating the heart, wherein when the heart rate decreases below a predetermined rate, said heart stimulator stimulates the heart at said predetermined rate.

10. A heart treatment equipment for treating a patient according to claim 1, wherein said controller terminates the generation of said nerve stimulation signal when the sensed intensity of the physical exercise or the mental stress sensed is lower than a predetermined level.

11. A heart treatment equipment for treating a patient according to claim 1, wherein said controller increases a strength of said nerve stimulation signal by adjusting a parameter of said nerve stimulation signal.

12. A heart treating method comprising:
   sensing an intensity of physical exercise or mental stress;
   selecting from a nerve stimulation parameter table a variable parameter suitable for said intensity of physical exercise or mental stress, in response to the sensed intensity of physical exercise or mental stress wherein said nerve stimulation parameter table relates the variable parameter to the sensed intensity; and
   stimulating a vagus nerve in accordance with the variable parameter, such that when the intensity of the physical exercise or the mental stress is relatively high, a relatively strong nerve stimulation is performed and when the intensity of the physical exercise or the mental stress is relatively low, a relatively weak nerve stimulation is performed or no nerve stimulation is performed.

13. A heart treating method according to claim 12, wherein said intensity of physical exercise or mental stress is sensed information of a heart.

14. A heart treating method according to claim 12, wherein said intensity of physical exercise or mental stress is sensed information of a signal that indicates autonomic nervous activity.

15. A heart treating method according to claim 12, wherein said parameter is at least one of a period between pulses, a pulse width, a number of pulses, a pulse current, a pulse voltage, a delay time, a rest time and a repetitive number or is a multiple combination chosen from these.

* * * * *